(12) United States Patent
Hamazaki

(10) Patent No.: US 6,988,981 B2
(45) Date of Patent: Jan. 24, 2006

(54) PROTECTIVE TOOL FOR THERAPEUTIC MATERIAL DELIVERY DEVICE, CARTRIDGE FOR THERAPEUTIC MATERIAL DELIVERY DEVICE, AND A THERAPEUTIC MATERIAL DELIVERY DEVICE

(75) Inventor: Kuniharu Hamazaki, Oita (JP)

(73) Assignee: Kawasumi Laboratories, Inc., Tokyo (JP)

( * ) Notice: Subject to any disclaimer, the term of this patent is extended or adjusted under 35 U.S.C. 154(b) by 0 days.

(21) Appl. No.: 10/727,554

(22) Filed: Dec. 5, 2003

(65) Prior Publication Data

US 2004/0122351 A1 Jun. 24, 2004

Related U.S. Application Data

(62) Division of application No. 10/013,366, filed on Dec. 13, 2001, now Pat. No. 6,723,037.

(30) Foreign Application Priority Data

| Dec. 15, 2000 | (JP) | ............................. 2000-381529 |
| Jul. 23, 2001 | (JP) | ............................. 2001-221182 |

(51) Int. Cl.
*A61N 5/00* (2006.01)
*A61M 5/32* (2006.01)

(52) U.S. Cl. ........................... 600/7; 604/192; 604/198; 604/263

(58) Field of Classification Search ................ 600/1–8; 250/506.1, 515.1; 414/146; 604/57, 110, 604/164.09, 263, 187, 192, 197, 198, 271, 604/272; 606/139, 213; 206/438
See application file for complete search history.

(56) References Cited

U.S. PATENT DOCUMENTS

| 3,073,306 | A | * | 1/1963 | Linder .......................... 604/198 |
| 4,122,836 | A | | 10/1978 | Burnett |
| 4,728,321 | A | * | 3/1988 | Chen ........................... 604/110 |
| 4,897,083 | A | * | 1/1990 | Martell ........................ 604/192 |
| 4,994,045 | A | | 2/1991 | Ranford |
| 5,059,185 | A | | 10/1991 | Ryan |
| 5,106,379 | A | | 4/1992 | Leap |
| 5,342,283 | A | | 8/1994 | Good |
| 5,460,592 | A | | 10/1995 | Langton et al. |

(Continued)

*Primary Examiner*—John P. Lacyk
(74) *Attorney, Agent, or Firm*—Oblon, Spivak, McClelland, Maier & Neustadt, P.C.

(57) ABSTRACT

A protective tool for a therapeutic material delivery device prevents wrong sticking of the outer needle of the device after use and prevents dissipation of blood adhering to the outer needle and comprises a cover (8'A) and a cap (61) or stopper (65) attached to a forward end of said cover for protecting the forward end of the outer tubular needle (2A), wherein said cover (8'A) is formed of a plurality of tubes (8'A1, 8'A2, 8'A3, . . . ) having different diameters that are formed so as to consecutively decrease from a forward place to the outer needle hub (2B) in a backward place, and said tubes are thereby connected such that the cover (8'A) is extendable in the longitudinal direction, and a cartridge for use with the therapeutic material delivery device permits direct calibration of a radioactive source charged therein and comprises a transparent cartridge body (8, 18, 38) that holds said therapeutic material (10) inside and permits external visual observation of the therapeutic material (10) and a shielding outer tube (9, 19, 39) that is fitted on an outer circumference of the cartridge body, is slidable in the longitudinal direction of said cartridge body and is made of a radioactive ray shielding material, said cartridge body (8, 18, 38) being exposable with said sliding of said shielding outer tube.

4 Claims, 21 Drawing Sheets

U.S. PATENT DOCUMENTS

| | | |
|---|---|---|
| 5,531,706 A | 7/1996 | de la Fuente |
| 5,906,574 A | 5/1999 | Kan |
| 5,993,427 A * | 11/1999 | Rolland et al. ............. 604/271 |
| 6,162,198 A * | 12/2000 | Coffey et al. ............... 604/198 |
| 6,221,003 B1 | 4/2001 | Sierocuk et al. |
| 6,358,195 B1 | 3/2002 | Green et al. |
| 6,450,937 B1 * | 9/2002 | Mercereau et al. ............ 600/7 |
| 6,723,037 B2 * | 4/2004 | Hamazaki et al. ............. 600/7 |
| 2002/0058854 A1 * | 5/2002 | Reed et al. ..................... 600/7 |
| 2002/0193808 A1 * | 12/2002 | Belef et al. ................. 606/139 |
| 2003/0036673 A1 * | 2/2003 | Schmidt ........................ 600/8 |

\* cited by examiner

PROTECTIVE TOOL FOR THERAPEUTIC MATERIAL DELIVERY DEVICE, CARTRIDGE FOR THERAPEUTIC MATERIAL DELIVERY DEVICE, AND A THERAPEUTIC MATERIAL DELIVERY DEVICE

This is a division of Application Ser. No. 10/013,366, now U.S. Pat. No. 6,723,037.

This application claims a priority based on Japanese Patent Application No.2000-381529 filed on Dec. 15, 2000 and No.2001-221182 filed on Jul. 23, 2001, the entire contents of which are incorporated herein by reference for all purposes.

BACKGROUND OF THE INVENTION

1. Field of the Invention

The present invention relates to improvements in therapeutic material delivery device (vehicle) for delivering (implanting) a therapeutic material such as a coiled or capsulated radioactive source to an organism for radiotherapy, for example, of a patient suffering prostate cancer.

2. Description of the Related Art

Radiotherapy (brachytherapy) refers to a treatment made by allowing a radioactive beam to radiate to a morbid tissue suffering a prostate cancer, an esophagus cancer, or the like. Radiotherapy includes high-dose, external beam radiation treatment and low-dose close-distance radiation treatment.

It is present practice to employ the latter method as a method for improving a therapeutical effect depending upon a therapeutic site and reducing side effects. In this case, there is practiced a method in which a radioactive source having radioactivity in the form of a sealed radioactive source is implanted (caused to remain) in a diseased part or a part near a morbid part with a delivery needle for the radioactive source, to treat the diseased part. The present invention is applied to the above method using the sealed radioactive source. The radioactive source for use in the present invention is selected from those containing radioactive isotopes that are clinically utilizable, and examples thereof include isotopes of cobalt, phosphorus, strontium, cesium, palladium, yttrium, iridium, rhenium, etc. Particularly preferred are isotopes that radiate β rays.

The above delivery needle is constituted of an inner needle member having a tubular needle and an outer needle member having a sticking needle formed to have a sharpened forward end, and a plurality of the capsular radioactive sources having radioactivity and having a size of approximately 5 mm are charged into the above outer needle member with tweezers. The above radioactive sources are spaced with spacers formed of a biodegradable substance, and a wax is applied to the forward end of the above sticking needle, so that the above radioactive sources do not come off the sticking needle.

When capsular radioactive sources are implanted in a diseased part with a delivery needle having the above sticking needle, approximately five radioactive sources are charged into one sticking needle as described above and are linearly implanted in the diseased part. In this manner, approximately 25 sticking needles above (corresponding to 125 radioactive sources) are embedded in different implantation positions. In the implantation, the implantation positions are secured while monitoring the positions with an ultrasonic diagnosis apparatus, so that the diseased part is uniformly irradiated with the radioactive sources.

Coiled radioactive sources formed by coiling rod-like or wire-like radioactive sources are recently used in place of capsular radioactive sources. That is because the coiled radioactive sources have a large surface area each and the length of the radioactive sources per piece can be increased as compared with the capsular radioactive sources, so that the number of the radioactive sources required can be decreased. The coiled radioactive sources are therefore less frequently charged into the outer needle member as compared with the capsular radioactive sources. Further, there is the merit of being free from spots that are not irradiated with a radioactive ray (cold spots), since it is not required to insert the spacers.

However, when a conventional inner needle member having a tubular needle and a conventional outer needle member having a sticking needle, which are used for implanting capsular radioactive sources, are used for implanting coiled radioactive sources in a diseased part, the coiled radioactive sources come to be curved, so that the irradiation with a uniform dose of radioactive ray can be no longer possible.

It is therefore required to prepare a medical sticking needle having a three-layered structure formed of an inner needle member through which coiled radioactive sources are to be passed or generally an inner needle member for holding a therapeutic material such as radioactive sources and extruding them forward, a middle needle member for fixing the radioactive sources and an outer needle member that is to be inserted into a diseased part or an intended portion, that is, a therapeutic material delivery device. The present invention relates to improvements in the above delivery device for delivering a therapeutic material such as radioactive sources.

Further, the delivery device may be a therapeutic material delivery device that is formed of an inner needle member for holding a therapeutic material such as radioactive sources and extruding them forward, a cartridge chargeable with the therapeutic material and an outer needle member that is to be inserted into a diseased part or an intended portion. The present invention also relates to improvements in such a delivery device using said cartridge.

SUMMARY OF THE INVENTION

It is an object of the present invention to provide a protective tool for a therapeutic material delivery device, which is for preventing wrong or accidental sticking of the outer needle after use and for preventing dissipation of blood adhering to the outer needle, and a delivery device having the tool.

It is another object of the present invention to provide a cartridge for use with a therapeutic material delivery device, which cartridge permits direct calibration of a radioactive source charged therein, and a delivery device having the cartridge.

It is still another object of the present invention to provide a cartridge for use with a therapeutic material delivery device, which cartridge is free from easy breakage of a connector tube connected to an outer needle of the delivery device, and a delivery device having the cartridge.

It is yet another object of the present invention to provide a cartridge for a therapeutic material delivery device, which cartridge permits extrusion of charged radioactive sources to the forward end of an outer needle without any resistance, and a delivery device having the cartridge.

It is further another object of the present invention to provide a cartridge for use with a therapeutic material delivery device, which cartridge permits calibration of the length of radioactive sources charged therein by easy external reading, and a delivery device having the cartridge.

Still further other objects of the present invention will be clear by descriptions to be made hereinafter.

According to the present invention, (1) there is provided a protective tool 68A or 68B for a therapeutic material delivery device comprising an outer needle 2 having an outer tubular needle 2A and an outer needle hub 2B supporting the outer tubular needle 2A, the protective tool being to be attached to said outer needle 2 for the protection thereof, the protective tool comprising a cover 8'A and a cap 61 or stopper 65 attached to a forward end of said cover for protecting the forward end of the outer tubular needle 2A, wherein said cover 8'A is formed of a plurality of tubes 8'A1, 8'A2, 8'A3, . . . having different diameters that are formed so as to consecutively decrease from a forward place to the outer needle hub 2B in a backward place, and said tubes are thereby connected such that the cover 8'A is extendable in the longitudinal direction.

According to the present invention, further, (2) there is provided a protective tool 68A for a therapeutic material delivery device as recited in the above (1), wherein said cap 61 has an inner tube 61A formed inside, said inner tube 61A has, made in a bottom thereof, a hole 62 for inserting and passing said outer tubular needle 2A, and said inner tube 61A has, formed in an outer circumference, a groove portion 63 for inserting a forward end of said outer tubular needle.

According to the present invention, further, (3) there is provided a protective tool 68B for a therapeutic material delivery device as recited in (1), wherein said stopper 65 is constituted of a tubular opening/closing portion 66 having a forward end and a connector portion 70, said opening/closing portion 66 has slits 71 formed in the longitudinal direction, one in an upper portion and the other in a lower portion, said forward end has an opening portion 66a, and said connector portion 70 has pressing portions 67 formed, one on the right and the other on the left, and has cutout grooves 69 formed, one in an upper place and the other in a lower place.

According to the present invention, further, (4) there is provided a protective tool 68A or 68B for a therapeutic material delivery device comprising an outer needle 2 having an outer tubular needle 2A and an outer needle hub 2B supporting the outer tubular needle 2A, a middle needle 3 having a middle tubular needle 3A and a middle needle hub 3B supporting the middle tubular needle 3A and an inner needle 4 having a solid needle 4A and an inner needle hub 4B supporting the solid needle 4A, the outer needle, the middle needle and the inner needle being to be connected for use, the protective tool being to be attached to said outer needle 2 for the protection thereof, which protective tool comprises a cover 8'A and a cap 61 or a stopper 65 that is attached to the forward end of said cover for protecting the forward end of said outer tubular needle 2A, wherein said cover 8'A is formed of a plurality of tubes 8'A1, 8'A2, 8'A3, . . . having different diameters that are formed so as to consecutively decrease from a forward place to the outer needle hub 2B in a backward place, and said tubes are thereby connected such that the cover 8'A is extendable in the longitudinal direction.

According to the present invention, further, (5) there is provided a protective tool 68A for a therapeutic material delivery device as recited in (4), wherein said cap 61 has an inner tube 61A formed inside, said inner tube has, in a bottom thereof, a hole 62 for inserting and passing said outer tubular needle 2A, and said inner tube 61A has, formed in an outer circumference thereof, a groove portion for inserting the forward end of said outer tubular needle 2A.

According to the present invention, further, (6) there is provided a protective tool 68B for a therapeutic material delivery device as recited in (4), wherein said stopper 65 is constituted of a tubular opening/closing portion 66 having a forward end and a connector portion 70, said opening/closing portion 66 has slits 71 formed in the longitudinal direction, one in an upper portion and the other in a lower portion, said forward end has an opening portion 66a, and said connector portion 70 has pressing portions 67 formed, one on the right and the other on the left, and has cutout grooves 69 formed, one in an upper place and the other in a lower place.

According to the present invention, further, (7) there is provided a therapeutic material delivery device 1A or 1B comprising an outer needle 2 having an outer tubular needle 2A and an outer needle hub 2B supporting the outer tubular needle 2A, wherein said outer needle 2 is covered with the protective tool 68A or 68B for a therapeutic material delivery device as recited in any one of (1) to (3), and the forward end of said outer tubular need 2A of said outer needle 2 is capped with a sheath 5' for protecting said forward end.

According to the present invention, further, (8) there is provided a therapeutic material delivery device 1A or 1B as recited in (7) wherein said sheath 5' has a projection 6' formed on an inner-circumference base portion thereof.

According to the present invention, further, (9) there is provided a therapeutic material delivery device 1A or 1B comprising an outer needle 2 having an outer tubular needle 2A and an outer needle hub 2B supporting the outer tubular needle 2A, a middle needle 3 having a middle tubular needle 3A and a middle needle hub 3B supporting the middle tubular needle 3A and an inner needle 4 having a solid needle 4A and an inner needle hub 4B supporting the solid needle 4A, said outer needle 2, said middle needle 3 and said inner needle 4 being to be connected in this order for use, wherein the protective tool 68A or 68B for a therapeutic material delivery device as recited in any one of (4) to (6) is attached to said outer needle 2.

According to the present invention, further, (10) there is provided a therapeutic material delivery device 1A or 1B as recited in (9), wherein said solid needle 4A is inserted in said middle tubular needle 3A, said middle tubular needle 3A is inserted in said outer tubular needle 2A and the forward end of said outer tubular needle 2A is capped with a sheath 5' for protection of said forward end.

According to the present invention, further, (11), there is provided a therapeutic material delivery device 1A or 1B as recited in (9) or (10), wherein said outer tubular needle 2A, said middle tubular needle 3A and said solid needle 4A are formed such that said solid needle 4A has a largest length, that said middle tubular needle 3A has an intermediate length and that said outer tubular needle 2A has a smallest length.

According to the present invention, further, (12) there is provided a therapeutic material delivery device 1A or 1B comprising a outer needle 2 having an outer tubular needle 2A and an outer needle hub 2B supporting the outer tubular needle 2A, a middle needle 3 having a middle tubular needle 3A and a middle needle hub 3B supporting the middle tubular needle 3A and an inner needle 4 having a solid needle 4A and an inner needle hub 4B supporting the solid needle 4A, wherein said outer needle 2, said middle needle 3 and said inner needle 4 are being to be connected for use.

According to the present invention, further, (13) there is provided a therapeutic material delivery device 1A or 1B as recited in (12), wherein the forward end of the outer tubular needle 2A of said outer needle 2 is capped with a sheath 5' for protection of said forward end.

According to the present invention, further, (14) there is provided a therapeutic material delivery device 1A or 1B as recited in (13), wherein said sheath 5' has a projection 6' formed on an inner circumference base portion thereof.

According to the present invention, further, (15) there is provided a therapeutic material delivery device 1A or 1B as recited in (12), wherein said outer tubular needle 2A, said middle tubular needle 3A and said solid needle 4A are formed such that said solid needle 4A has a largest length, that said middle tubular needle 3A has an intermediate length and that said outer tubular needle 2A has a smallest length.

According to the present invention, further, (16) there is provided a cartridge 7,17 or 37 for a therapeutic material delivery device, which cartridge permits external visual observation of the therapeutic material, the cartridge comprising a transparent cartridge body 8, 18 or 38 that holds said therapeutic material 10 inside and permits external visual observation of the therapeutic material 10 and a shielding outer tube 9, 19 or 39 that is fitted on an outer circumference of the cartridge body, is slidable in the longitudinal direction of said cartridge body and is made of a radioactive ray shielding material, said cartridge body 8, 18 or 38 being exposable with said sliding of said shielding outer tube.

According to the present invention, further, (17) there is provided a cartridge 7 or 17 for a therapeutic material delivery device as recited in (16), wherein the forward end of said cartridge body 8 or 18 is provided with a head portion 5 or 5A, a connector tube 6 is supported through said head portion, and said connector tube 6 is capped with a sheath 12 having an opening portion 12A formed therein.

According to the present invention, further, (18) there is provided a cartridge 37 for a therapeutic material delivery device as recited in (16), wherein the forward end of said cartridge body 38 is provided with a head portion 5E, a connector tube 36 is supported through said head portion and said connector tube 36 is capped with a cap C1 having a protection portion 21 and a spindle rod 22 supported on a central portion of inner circumference end portion of the protection portion 21.

According to the present invention, further, (19) there is provided a cartridge 7 or 37 for a therapeutic material delivery device as recited in any one of (16) to (18), wherein an engagement portion 5C or 35C is formed in the backward end of the head portion 5 or 5E provided in the forward end of said cartridge 7 or 37, an engagement portion 9A or 38A is formed in the forward end of said outer tube 9 or 39, and these engagement portions are engageable with each other.

According to the present invention, further, (20) there is provided a cartridge 7, 17 or 37 for a therapeutic material delivery device as recited in any one of (16) to (19), wherein a stopper 16 is attached to nearly a central portion of said head portion 5, 5A or 5E of said cartridge body 8, 18 or 38, and said cartridge body and said outer tube are engageable with each other on the basis of a frictional resistance between said stopper 16 and an inner circumference of forward end of said outer tube 9, 19 or 39.

According to the present invention, further, (21) there is provided a cartridge 7 or 17 for a therapeutic material delivery device as recited in any one of (16), (17), (19) and (20), wherein an outer circumference surface of said cartridge body 8 or 18 is provided with a scale 20 for checking a length or an amount of the therapeutic material 10 charged inside said cartridge body 8 or 18.

According to the present invention, further, (22) there is provided a cartridge 37 for a therapeutic material delivery device as recited in any one of (16), (18), (19) and (20), wherein an outer circumference surface of said cartridge body 38 is provided with a scale 30 having divisions starting at 0 cm at intervals of 1 cm for checking a length of the therapeutic material 10 charged in said cartridge body 38 and for calibration of the entire therapeutic material 10.

According to the present invention, further, (23) there is provided a cartridge 27 for a therapeutic material delivery device, which cartridge has a cartridge body 28 that permits external visual observation of a therapeutic material 10 held therein, wherein said cartridge body 28 is formed of material that can work as a shield against radioactive rays and has a scale 20 provided on an outer circumference of said cartridge body 28, the forward end of said cartridge body 28 has a head portion 5B, a connector tube 6 is supported through said head portion, and said connector tube 6 is capped with a sheath 12 having an opening portion 12A formed therein.

According to the present invention, further, (24) there is provided a therapeutic material delivery device 1 comprising an outer needle 2 or 32 having an outer tubular needle 2A or 32A and an outer needle hub 2B or 32B supporting the outer tubular needle 2A or 32A, the cartridge 7, 17, 27, 37 for a therapeutic material delivery device as recited in any one of (16) to (23) which cartridge is chargeable with a therapeutic material 10 and an inner needle 4 having a solid needle 4A and an inner needle hub 4B supporting the solid needle 4A, wherein an inner circumference of said outer needle hub 2B or 32B and the forward end portion of said cartridge 7, 17, 27 or 37 are formed to have mutually engageable forms, the therapeutic material delivery device 1 having a constitution in which said solid needle 4A is inserted through the backward end of said cartridge 7, 17, 27 or 37 thereby to extrude said therapeutic material 10 into said tubular needle 2A or 32A with the forward end of said solid needle 4A.

BRIEF DESCRIPTION OF THE DRAWINGS

FIG. 2(a) is a schematic drawing of an outer needle 2, FIG. 2(b) is a schematic drawing of a middle needle, and FIG. 2(c) is a schematic drawing of an inner needle.

FIG. 8(a) is a front view, and FIG. 8(b) is a plan view.

FIG. 12(A) is a side view of forward end of an outer tube 9, FIG. 12(B) are a cross-sectional view of the outer tube 9 in the longitudinal direction, and FIG. 12(C) is a schematic drawing of a cartridge body 8.

DESCRIPTION OF THE PREFERRED EMBODIMENTS

The present invention will be explained in detail hereinafter.

(Therapeutic Material Delivery Device)

The "therapeutic material" in the present invention refers to a tumor-treating material against tumors such as cancers. The protective tool for a therapeutic material delivery device, provided by the present invention, is a tool that is used with a therapeutic material delivery device. The therapeutic material delivery device may be a double-layer-structured delivery device having at least an outer needle 2 formed of an outer tubular needle 2A and an outer needle hub 2B supporting the outer tubular needle 2A, and an inner needle 4 formed of a solid needle 4A and an inner needle hub 4B supporting the solid needle 4A as shown in part of FIG. 1. Preferably, the therapeutic material delivery device is a three-layer-structured therapeutic material delivery device 1 having an outer needle 2 formed of an outer tubular needle 2A and an outer needle hub 2B supporting the outer tubular needle 2A, a middle needle 3 formed of a middle tubular needle 3A and a middle needle hub supporting the middle tubular needle 3A and an inner needle 4 formed of a solid needle 4A and an inner needle hub 4B supporting the solid needle 4A as is shown in the entire drawing of FIG. 1. And, the outer needle 2, the middle needle 3 and the inner needle 4 are connected in this order when used.

(Outer Needle and Sheath 5')

Figure 3:
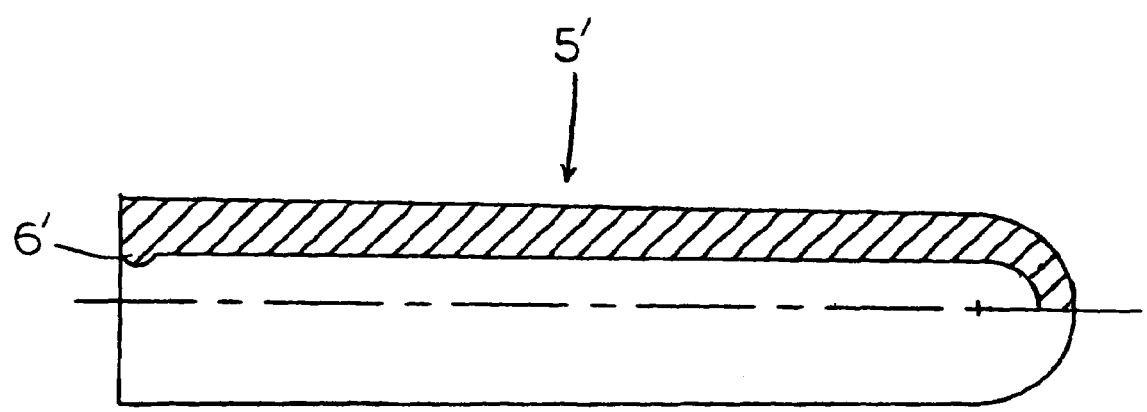
FIG. 3 is a schematic partial exploded drawing of a sheath 5'.

The therapeutic material delivery device 1 (to be sometimes abbreviated as "delivery device 1" hereinafter) of the present invention has at least an outer needle 2 formed of an outer tubular needle 2A and an outer needle hub 2B supporting the outer tubular needle 2A. The outer tubular needle 2A of the outer needle 2 is preferably made of a metal such as SUS304, SUS316, or the like, and the forward end portion thereof is formed so as to have a sharpened end for sticking it into a human body. The forward end of the above outer tubular needle 2A of the outer needle 2 is covered with a sheath 5'. The sheath 5' is provided for protecting the sharp forward end of the outer tubular needle 2A. That is, when the forward end of the outer tubular needle 2A of the delivery device is capped with the sheath 5', the sheath 5' can prevent a bending (curling) of the forward end of the outer tubular needle 2A which bending (curling) may be caused by a contact of the forward end to a surface of a storage box or a delivery plate to be described later. Preferably, the sheath 5' is made of an elastic material. For example, the elastic material includes synthetic rubbers such as isoprene rubber, chloroprene rubber, acryl rubber, silicone rubber and nitrile rubber; and synthetic resins such as polyolefin resins, polyurethane resins, polyester resins and polyvinyl chloride rubbers, which are thermoplastic elastomers. Preferably, a projection 6' is formed on a base part of inner circumference of the sheath 5' as shown in FIG. 3. The above projection 6' is formed for contact-fixing the projection 6' to the outer circumferential wall of the above outer tubular needle 2A, so that the covering sheath 5' does not easily come off the outer tubular needle 2A.

The above outer needle 2, the middle needle 3 and the inner needle 4 are connected in this order when used. Specifically, the solid needle 4A of the inner needle 4 is inserted into, and positioned in, the above middle tubular needle 3A, and the above middle needle 4 is inserted into, and positioned in, the outer tubular needle 2A of the above outer needle 4.

(Outer Tubular Needle Marker)

Figure 1:
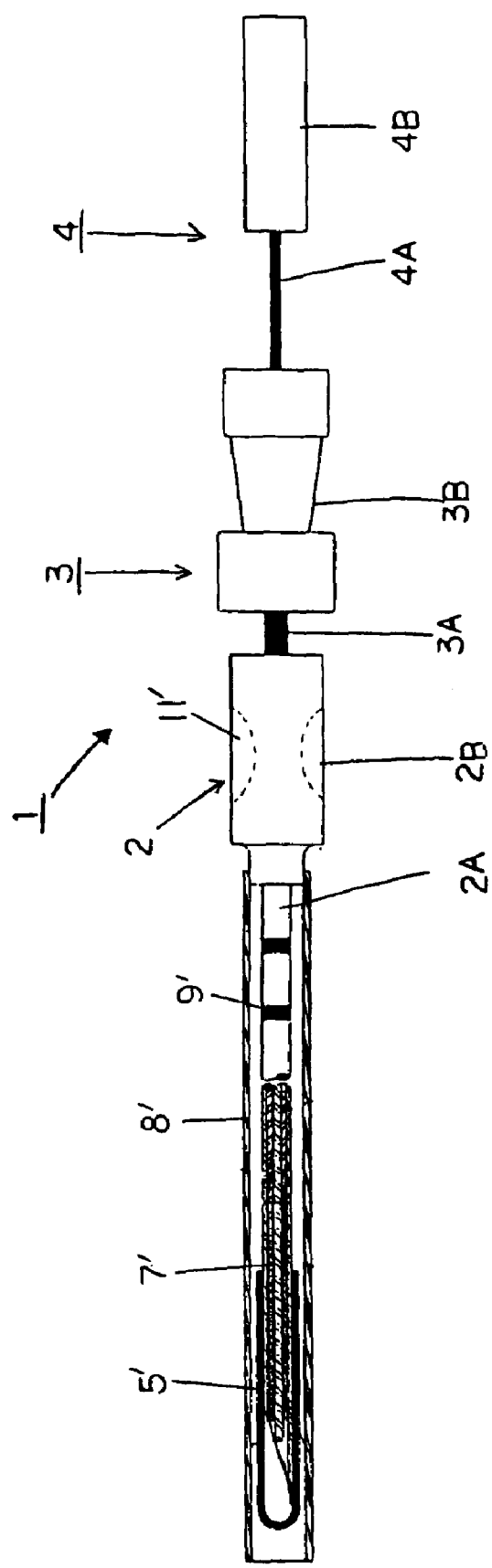
FIG. 1 is a schematic drawing of one example of the therapeutic material delivery device 1 of the present invention.

Preferably, the outer circumference of the above outer tubular needle 2A has markers 9' that are provided equivalently as indices for a length of insertion of the outer tubular needle 4 into a diseased part or withdrawal thereof from the diseased part, as is shown in FIG. 1. Preferably, for example, dented portions 11' are formed in the outer circumference of the outer needle hub 2B, so that an operator easily manually handles the delivery device. Further, preferably, a marker 10' is provided on the outer circumference of the outer needle hub 2B for indicating the direction of edge surface of the forward end of the above outer tubular needle 2A as shown in FIG. 2(a).

(Middle Needle)

Figure 2:
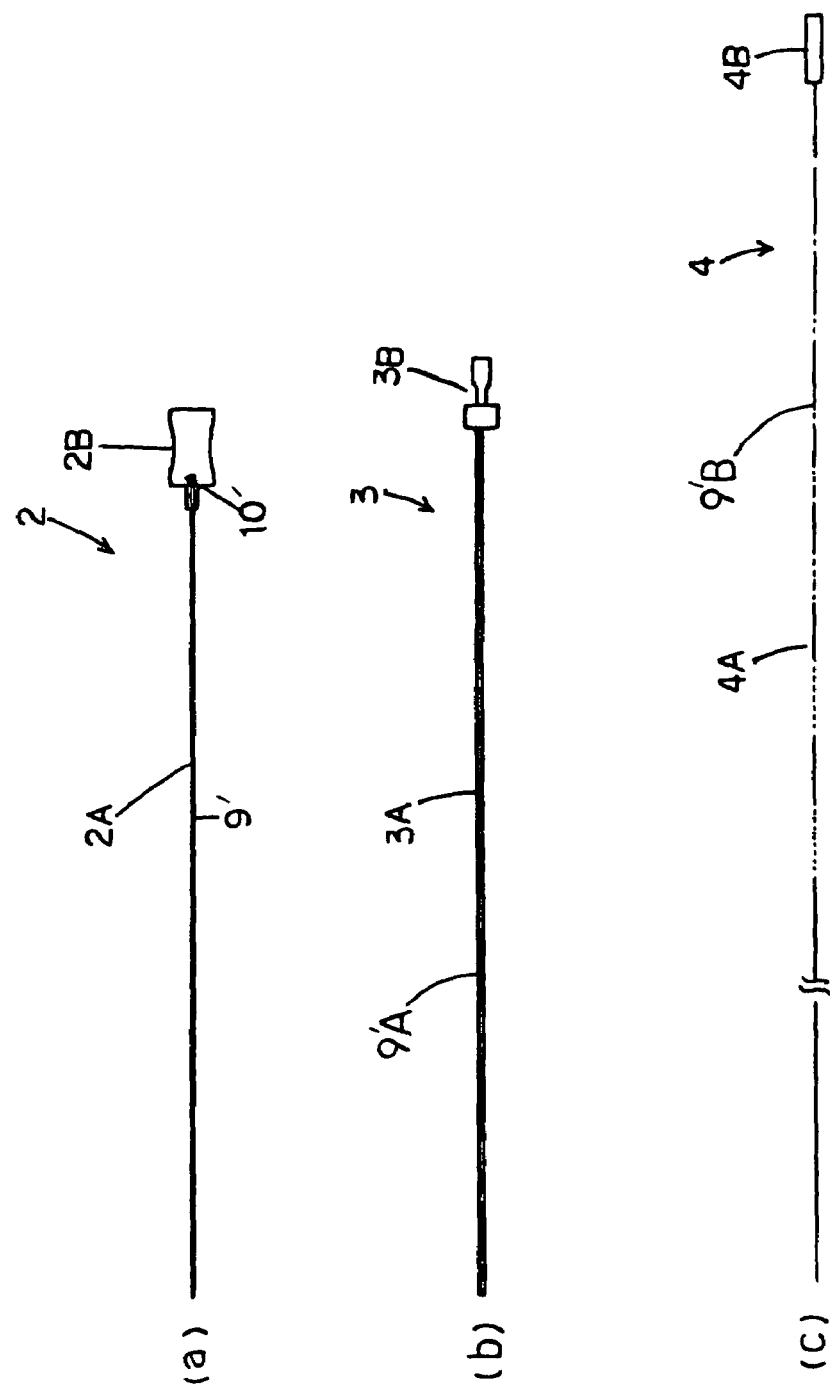
FIGS. 2(a), 2(b) and 2(c) are exploded views of the therapeutic material delivery device shown in FIG. 1.

Like the above outer needle hub 2A, the middle tubular needle 3A of the middle needle 3 is made of a metal such as SUS304, 316, or the like, and it has the form of a tube and the forward end thereof is formed to be flat as shown in FIG. 2(b). Once a radioactive source 7, is arranged around the forward circumference of the above solid needle 4A, the backward movement of the radioactive source 7' can be prevented since the forward end of the above middle tubular needle 3A is present.

On the outer circumference of each of the middle tubular needle 3A and the inner needle 4A, further, markers 9'A (or 9'B) are provided at equal intervals as shown in FIGS. 2(b) or 2(c). The markers 9'A on the middle tubular needle 3A indicate positions of the forward end of the middle needle 3 when it is inserted into the outer needle 2. Further, the markers 9'B on the inner needle 4A can work as an index for aligning the forward end of the radioactive source 7' and the forward end of the inner needle 4 by longitudinally moving the above inner needle 4.

The above markers 9'A (and 9'B) can be provided on the above circumferences so that the number of the markers shows an actual length, like, for example, 1 cm shown by one marker or 2 cm shown by two markers.

(Inner Needle)

The solid needle 4A of the inner needle 4 is generally made of a metal such as SUS304, 316, or the like, and is formed to have the form of a fine wire. While the solid needle 4A preferably has the form of a wire, it may be a so-called tubular pin (sometimes referred to as "pipe-shaped pin" hereinafter) having a hollow portion inside, so long as the solid needle 4A can fit (the term "insert" is sometimes used hereinafter) the radioactive source 7 to the forward end of the outer circumference or extrude a capsulated radioactive source charged inside the outer needle from the outer needle so that the radioactive source can be implanted in an intended part in a human body. The solid needle 4A in the present invention therefore includes both a solid needle having the form of a wire and a solid needle having the form of a tube.

(Assembly of Delivery Device)

The delivery device 1 of the present invention has a form shown in FIG. 1, and for example, it is assembled as follows. First, the above solid needle 4A is inserted into, and positioned in, the above middle tubular needle 3A through the above middle needle hub 3B. Further, the above middle tubular needle 3A is inserted into, and positioned in, the above outer tubular needle 2A through the above outer needle hub 2B, to assemble the delivery device 1 having a three-layer structure. In the above three-layer-structured delivery device, the sheath 5' is fitted on the forward end of the outer needle 2, and a cover 8' as a protective tool (to be described later) for the delivery device is fitted to the above outer tubular needle 2A, for the protection of the delivery device.

In the present invention, in compliance with the constitution of the above three-layer-structured delivery device, the above outer tubular needle 2A, the above middle tubular needle 3A and the above solid needle 4A are formed such that the solid needle 4A has a largest length, that the middle tubular needle 3A has an intermediate length and that the outer tubular needle 2A has a smallest length, as shown in FIGS. 2(a), 2(b) and 2(c).

In the present invention, when the coil-shaped radioactive source 7' is implanted in a diseased part or an intended part, the coil-shaped radioactive source 7' can be linearly implanted without curving the coil-shaped radioactive source 7', owning to the use of the delivery device 1 formed of the inner needle 4, the middle needle 3 and the outer needle 2 in which the solid needle 4A having a largest length, the middle tubular needle 3A having an intermediate length and the outer tubular needle 2A having a smallest length are arranged in this order.

In this case, when the middle needle 3 is inserted into the outer needle 2 thereby to align the middle needle hub 3B of the middle needle 3 and the outer needle hub 2B of the outer needle 2, preferably, the middle tubular needle 3A of the middle needle 3 is exposed from the edge surface of the outer tubular needle 2A of the outer needle 2 to some extent. That is because the radioactive source 7' charged in the solid needle 4A of the inner needle 4 can be completely exposed from the forward end of the outer tubular needle 2A of the above outer needle 2. If the forward end of the middle tubular needle 3A of the middle needle 3 is not exposed from the edge surface of the outer tubular needle 2A of the outer needle 2, the backward portion of the radioactive source 7' may be caught inside the outer tubular needle 2A of the outer needle 2, so that it may be difficult to conduct an implanting operation.

The solid needle 4A of the inner needle 4 is required to have a length that is equivalent approximately to at least the total length of the middle needle 3 and the radioactive source 7' for exposing the radioactive source 7' from the forward end of the outer tubular needle 2A of the above outer needle 2, so that the solid needle 4A has the largest length among the above three needle types.

(Method of Using Delivery Device)

A typical example of the method of use of the delivery device 1 of the present invention for low-dose radiation treatment will be explained below.

(1) The middle needle 3 and the inner needle 4 are integrally withdrawn from the outer needle 2 of the delivery device 1 shown in FIG. 1.

(2) In this case, the solid needle 4A of the inner needle 4 is exposed from the middle tubular needle 3A of the middle needle 3.

(3) The coil-shaped radioactive source 7' is charged around the forward end of the solid needle 4A in the above (2). In other words, the forward end portion of the solid needle 4A is inserted into the coil-shaped radioactive source 7'.

(4) After it is made certain that the above solid needle 4A is kept inserted through the radioactive source 7', the middle needle 3 and the inner needle 4 are integrally inserted into the outer needle 2 capped with the sheath 5', and the insertion is continued until the forward end of the above solid needle 4A comes in contact with the sheath 5'.

(5) The delivery device 1 charged with the radioactive source 7 is stored in a storage box (not shown) without a cover 8'. The storage box is a container that has holes which are arranged in width and longitudinal directions and into which delivery devices 1 are regularly inserted, and the container is used for temporary storage of the delivery devices before sticking needles of the delivery devices charged with the radioactive source each are inserted to diseased parts of patients.

(6) When the radioactive source 7' is stuck into a diseased part or an intended portion, generally, radioactive sources are implanted with a plate (not shown) having sticking holes arranged regularly in the longitudinal and width directions. The outer needles 2 of the delivery devices 1 taken out of the storage box are stuck in the sticking holes (intended positions) of the plate that determines implantation positions. The outer needle 2 brakes through the sheath 5' to reach an intended portion of a patient. In this case, preferably, implantation positions are checked with monitoring them with an ultrasonic diagnosis apparatus inserted through an anus in the same manner as in the implantation positioning of a conventional capsulated radioactive source.

(7) After the implantation positions are determined, the middle needle hub 3B of the middle needle 3 of the delivery device 1 is fixed to be still, and the outer needle 2 is withdrawn backward, whereby the radioactive source 7' charged in the solid needle 4A of the inner needle 4 is exposed inside a body.

(8) The middle needle hub 3B of the middle is fixed to be still, and the inner needle hub 4B of the inner needle 4 is withdrawn, whereby the radioactive source 7' is linearly implanted in an intended portion in the body.

(9) The outer needle 2 and the middle needle 3 are withdrawn at the same time, to complete the implantation of the radioactive source 7'.

While the three-layer-structured delivery device 1 having the forward end of the outer tubular needle 2A capped with the sheath 5' has been explained above with reference to its use example, a delivery device having the outer needle charged with a conventional capsulated radioactive source (delivery device having an outer needle formed of an outer tubular needle and an outer needle hub supporting the outer tubular needle) having the forward end of the outer needle 2 capped with the sheath 5' can be similarly used.

(Protective Tool for Therapeutic Material Delivery Device and Method of Use Thereof)

Figure 4:
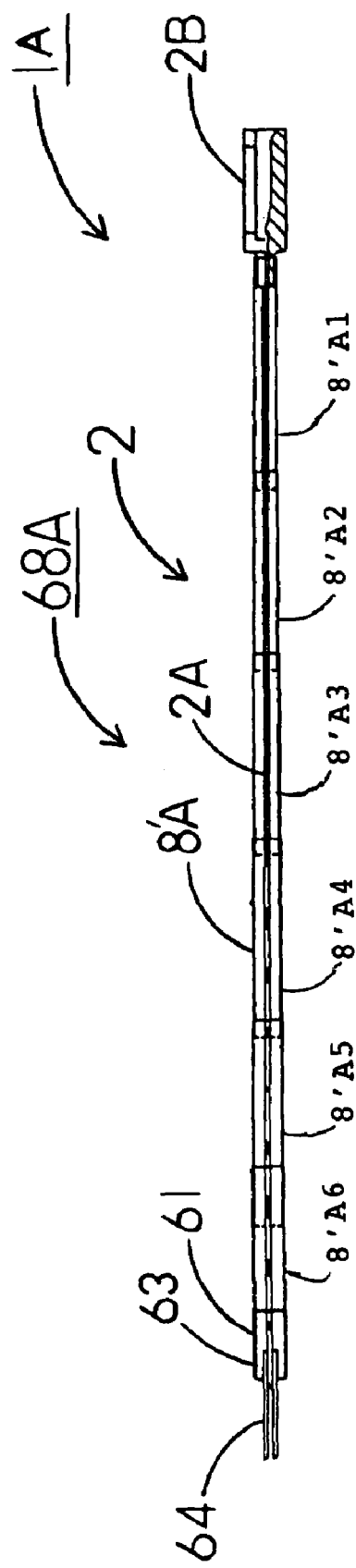
FIG. 4 is a schematic drawing of a delivery device 1A in which a forward end cover 64 is attached to a protective tool 68A.
Figure 5:
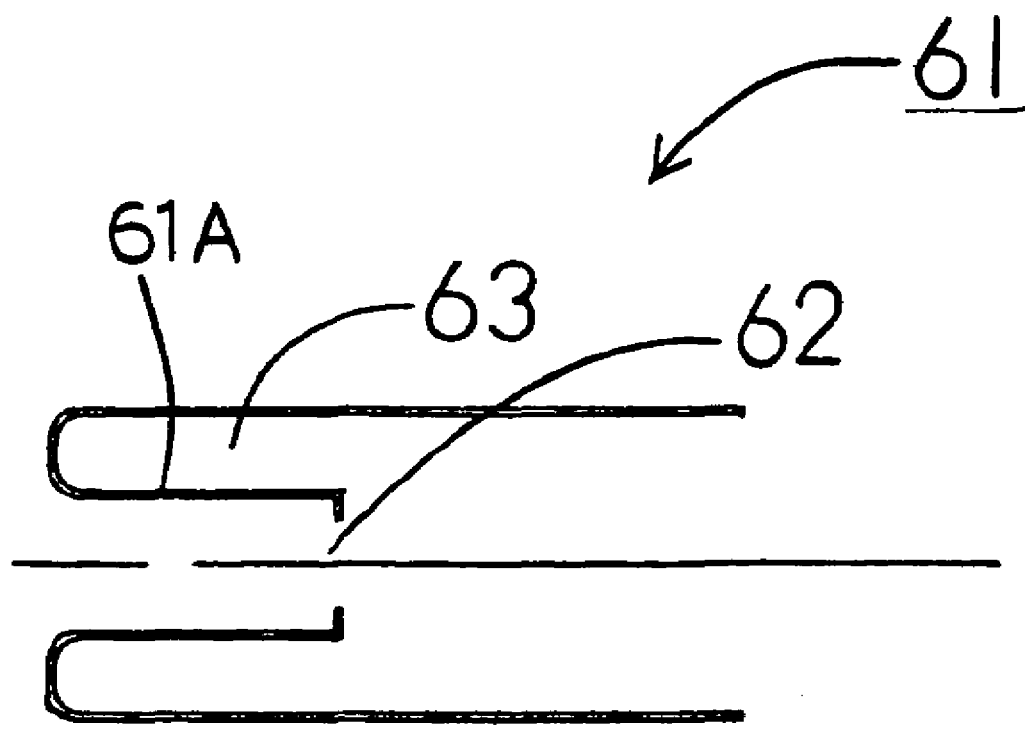
FIG. 5 is a cross-sectional view of a cap 61.

FIG. 4 is a schematic drawing of a delivery device 1A to which a protective tool 68A for a therapeutic material delivery device (to be sometimes abbreviated as "protective tool 68A" hereinafter) is fitted, provided by the present invention. FIG. 5 is a cross-sectional view of a cap 61 for use as an element of the protective tool. The above protective tool can be applied both to the three-layer-structured delivery device and the delivery device having the inner needle and the outer needle and having a capsulated radioactive source charged in the outer needle.

The above protective tool 68A is constituted of a cover 8' for covering the outer tubular needle 2A and a cap 61. Preferably, the forward end of the outer tubular needle 2A is covered with a pipe-shaped forward end cover 64 for protecting the needle end before use.

The above cover 8' is formed of a plurality of tubes having different diameters (8'A1, 8'A2, 8'A3, . . . , 8'An) as shown in FIG. 4. In order to make a good connection with the cap 61 and forward end cover 64 and allow a smooth move forward of the outer tubular needles 2A, the tubes are formed such that the diameters thereof consecutively decrease from a forward place to the outer needle hub in a backward place (8'An> . . . >8'A3>8'A2>8'A1), whereby the tubes are connected in such a manner that the tubes are extended and shrunk (folded) in the longitudinal direction of the tubes. In addition, n represents the number of the tubes, and a proper number can be selected depending upon the length of the outer tubular needle 2A. It is not excluded that if necessary the diameters of the tubes may be constructed in the opposite mode as described above (8'An< . . . <8'A3<8'A2<8'A1).

When the above cover 8'A is used to cover the outer tubular needle 2A, the innermost tube (8'A in this case) having the smallest diameter is fitted to the outer needle hub 2B of the outer needle 2 and the cover 8' is extended in the direction of the needle forward end. In this manner, there is formed a tube that changes stage by stage from a smallest tube member to a largest tube member. FIG. 4 shows a state of the thus-formed multi-stage tube, for example, a six-staged tube (tube members 8'A1, 8'A2, 8'A3, 8'A4, 8'A5 and 8'A6) covering the outer tubular needle 2A.

Further, the forward end of the above cover 8'A is capped with a cap 61. As shown in FIG. 5, the above cap 61 has an inner passage 61A formed inside, and a bottom of the inner passage 61A has a hole for passing the above outer tubular needle 2A through it. Further, a circumference of the inner passage 61A has a groove 63 for inserting the above outer tubular needle 2A therein for rest.

Figure 6:
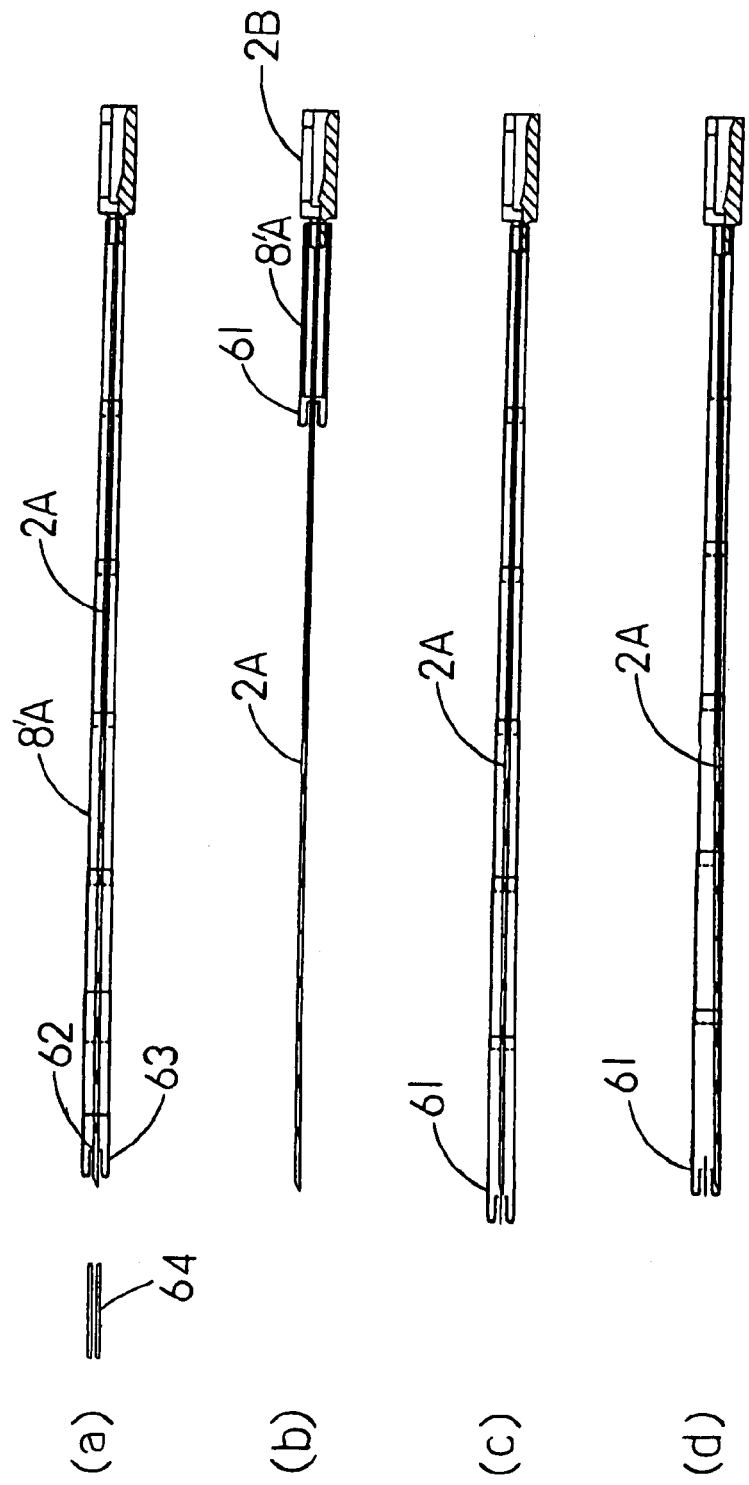
FIGS. 6(a), 6(b), 6(c) and 6(d) are schematic drawings for showing how to use the protective tool 68A attached to the delivery device 1A in FIG. 4.

FIG. 6 shows one example showing how to use the delivery device 1 to which the protective tool 68A having the cap 61 in its forward end is attached. The method of using the delivery device 1 will be explained with reference to FIG. 6 hereinafter.

(1) The forward end cover 64 attached to the above delivery device 1A is removed (FIG. 6(a)).

(2) The cap 61 and the cover 8' are pushed toward the outer needle hub 2B to fold the cover 8'A and to expose the outer tubular needle 2A (FIG. 6(b)).

(3) The radioactive source 7' is implanted in an intended portion in a body with the delivery device according to the already explained method.

(4) After the use of the delivery device (after completion of the implantation of the radioactive source), the above cover 8'A is extended to encase the forward end of the outer tubular needle 2A in the cap 61 (FIG. 6(c)).

(5) The outer-circumferential portion of the outer tubular needle 2A is brought into contact with the cap 61 and the inner circumference (inner wall) of the cover 8'A, and then the above cover 8'A is pushed toward the outer needle hub 2B, to insert the forward end of the outer tubular needle 2A in the groove 63 of the above cap 61 for rest.

The protective tool 68A is covered on the outer needle 2 as described above, whereby wrong or accidental sticking with the used outer tubular needle 2A and dissipation of adhering blood can be prevented.

(Other Embodiment of the Protective Tool)

Figure 7:
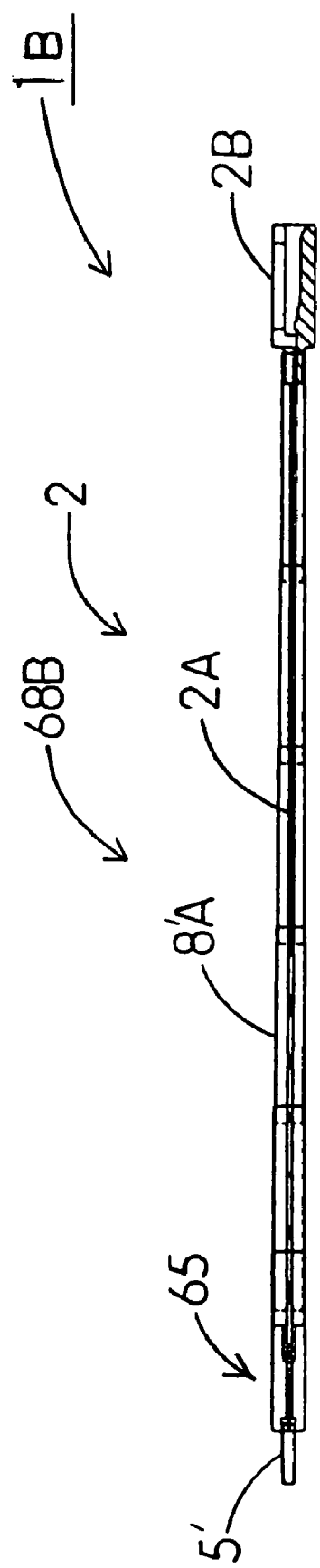
FIG. 7 is a schematic drawing of a delivery device 1B in which a sheath 5' is attached to a protective tool 68B.

FIG. 7 is a schematic drawing of a delivery device 1B using a protective tool 68B for a therapeutic material delivery device (to be sometimes referred to as "protective tool 68B" hereinafter) which protective tool is other embodiment of the present invention different from the above protective tool 68A (FIG. 4).

Figure 8:
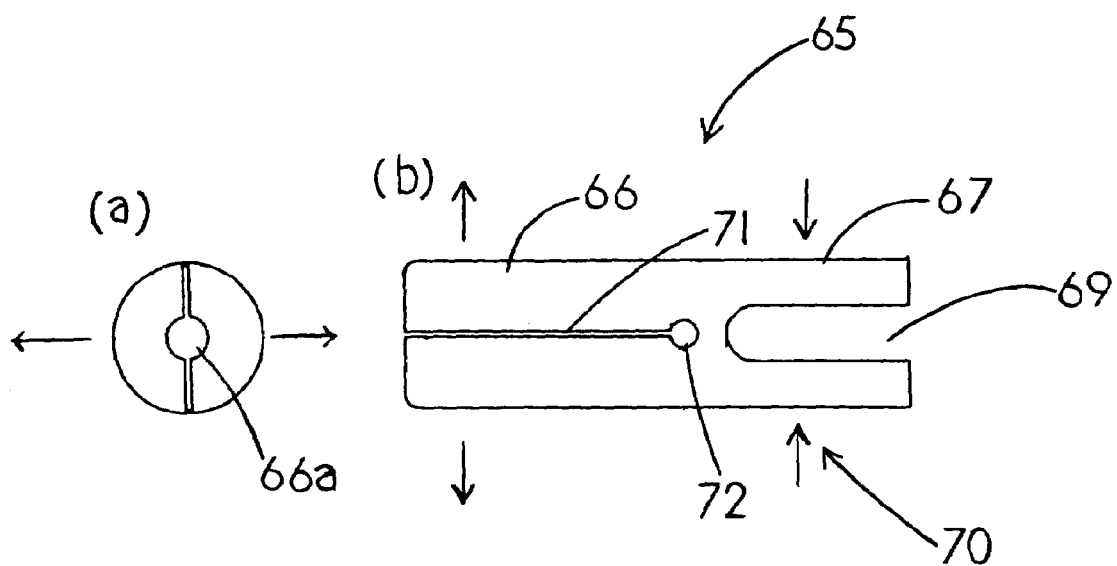
FIGS. 8(a) and 8(b) are schematic drawings of a stopper 65.

FIG. 7 shows the delivery device 1B to which the protective tool 68B and the sheath 5' are attached. The delivery device 1B can be applied to both a three-layer-structured delivery device and a delivery device having an inner needle and an outer needle and having a capsulated radioactive source charged in the outer needle. FIGS. 8(a) and 8(b) are schematic drawings of a stopper 65; FIG. 8(a) is a front view, and FIG. 8(b) is a plan view.

The above protective tool 68B is constituted of the above cover 8'A and a stopper 65, and the forward end of the above stopper 8'A is capped with the stopper 65. The above stopper is arranged such that a slit 71 and a cutout groove 69 to be described later are positioned above and below.

In the above stopper 65, a tubular opening/closing portion 66 having a forward end and a connector portion 70 are integrally formed.

In the above opening/closing portion 66, slits 71 are formed in the longitudinal direction, one in an upper portion and the other in a lower portion. As shown in FIG. 8(a), further, an opening portion 66a communicating with the slits 71 and having the form, for example, of a circle is formed in the above forward end portion. Further, in a backward place of the above slits 71, a hole 72 having the form, for example, of a circle and communicating with the slits 71 is formed (FIG. 8(a)). While the above slits 71 may have a slight width each, the slits 71 may be a parting cut. In the above connector portion 70, pressing portions 67 are formed, one on the right and the other on the left, and cutout grooves 69 are formed, one in an upper place and the other in a lower place. The stopper 65 is fitted to the forward end of the cover 8'A such that the slits 71 and the cutout grooves 69 are positioned one each top and bottom. When the above pressing portions 67 are held with fingers and pressed toward each other, the opening/closing portion 66 opens fanwise along the slits 71 from the hole 72 as a center, whereby the above opening portion 66a also opens leftward and rightward. When the pressing force is decreased, the above opening/closing portion 66 closes, and at the same time, the above opening portion 66a also closes.

Further, as shown in FIG. 7, the forward end of the outer tubular needle 2A is capped with the sheath 5', and the outer circumference of the above sheath 5' is held between opening portions 66a of the opening/closing portion 66 of the above stopper, so that the sheath 5' does not come off the forward end of the outer tubular needle 2A.

Figure 9:
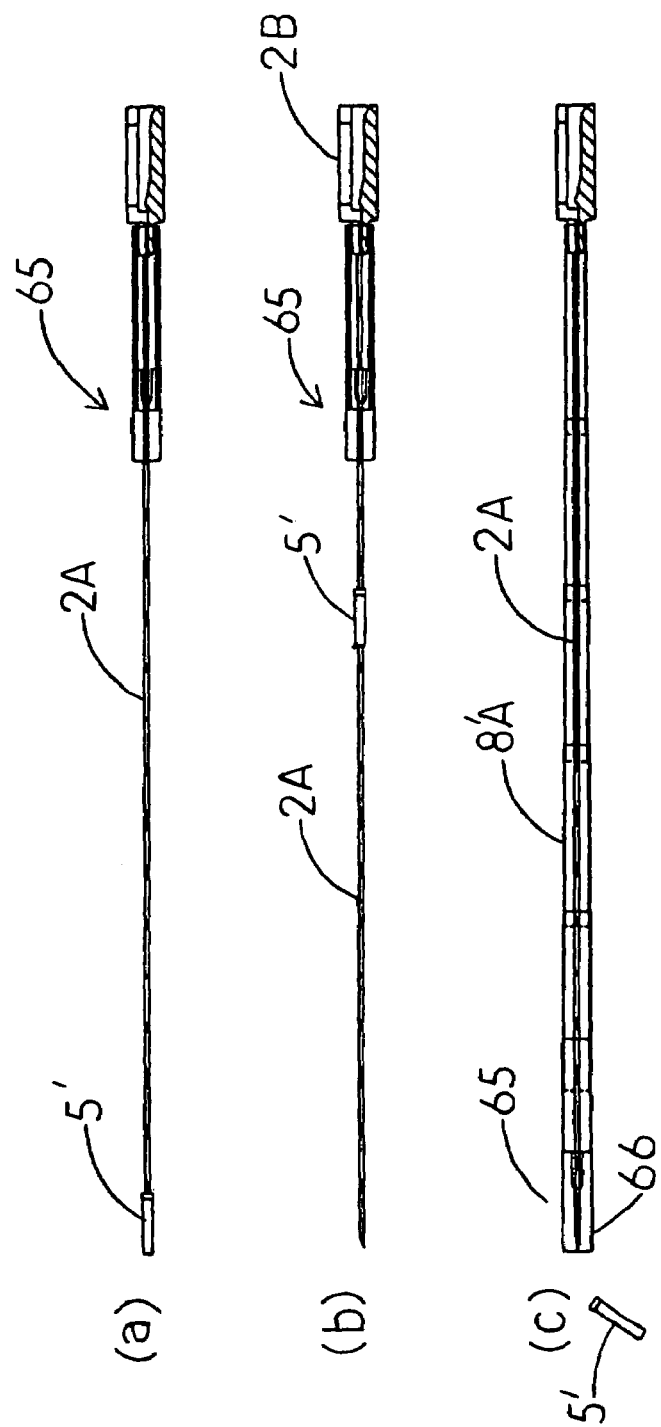
FIGS. 9(a), 9(b) and 9(c) are schematic drawings for showing how to use the protective tool 68B attached to the delivery device 1B in FIG. 7.

FIG. 9 shows one example of the method of use of the delivery device 1B to which the protective tool 68B having the stopper 65 in its forward end is attached. The method of use will be explained with reference to FIG. 9 hereinafter.

(1) As shown in FIG. 7, the sheath 5' is held between the opening portions 66a of the stopper 65 during the storage of the delivery device. In this state, the pressing portions 67 of the above stopper 65 are pressed with fingers to open the opening/closing portion 66, and the outer circumference of the sheath 5' is removed from the opening portions 66a. The above cover 8'A is folded toward the outer needle hub 2B to expose the outer tubular needle 2A (FIG. 9(a)).

(2) The radioactive source 7' is implanted in an intended portion in a body with the delivery device 1B according to the already explained method.

(3) After the delivery device is used (after the implantation of the radioactive source is completed), the sheath 5' is moved to have a position nearly in a central portion of the tubular needle 2A (FIG. 9(b)).

(4) The stopper 65 and the cover 8'A are moved toward the forward end of the tubular needle 2A, and the above sheath 5' is removed from the outer tubular needle 2A to place the forward end of the outer tubular needle 2A in the opening/closing portion 66 of the stopper 65 (FIG. 9(c)).

In this manner, as shown in the above-referenced FIG. 9(c), the outer tubular needle 2A encased in the protective tool 68B has only one end supported with the outer needle hub and the other end (forward end) is not supported, so that the outer tubular needle 2A bends due to its own weight to have its forward end portion coming close to the inner wall of the above protective tool 68B. In this manner, there is no case where the forward end of the above outer tubular needle 2A is exposed from the opening portions 66a of the stopper 65.

When the protective tool 68B is used to cover the outer needle 2 as described above, therefore, wrong or accidental sticking with the used outer tubular needle 2A and dissipation of adhering blood can be prevented.

The above cover 8'A, the above cap 61 and the above stopper 65 can be formed from a hard plastic such as polycarbonate, polymethyl methacrylate, polypropylene or polyvinyl chloride or an easily processible metal such as stainless steel or aluminum. As explained above, the protective tools 68A and 68B for a therapeutic material delivery device, provided by the present invention, can be suitably applied, for example, to the delivery devices 1, 1A and 1B for delivery (implantation) of the therapeutic material such as a radioactive source.

(Delivery Device Using Transparent Cartridge)

The therapeutic material delivery device may be a therapeutic material delivery device that is constructed according to a method somewhat different from the above-explained method. The device comprises an inner needle for holding a therapeutic material and extruding it forward, a transparent cartridge chargeable with a therapeutic material, and an outer needle to be stuck into a diseased part or an intended portion.

For a basic therapeutic material delivery device using such a cartridge, the present applicants have already filed Japanese Patent Application No. 2001-068695.

In this case, however, the radiation dose of a radioactive source is calibrated (checked) before the radioactive source is charged into the cartridge. Therefore, the radioactive source is inevitably calibrated in a state where it is exposed.

Further, since the cartridge has the form of a nearly ellipsoid like a pencil cap and is formed of lead glass or a burst-resistant resin, the forward end thereof may be broken when a force is laterally exerted on the cartridge that is attached to the outer needle hub of the outer needle.

In the above cartridge, further, the cartridge is stuffed with a filler in the forward and backward ends so that the charged radioactive source does not come out. When the amount of the filler is large, the filler is liable to enter the outer needle hub, and if this is case, it is difficult to extrude the radioactive source to the forward end of the outer tubular needle. According to the present invention, there is provided a delivery device for use with the above cartridge, which delivery device overcomes the problem caused by the use of the above cartridge.

The delivery device will be explained with reference to drawings.

Figure 10:
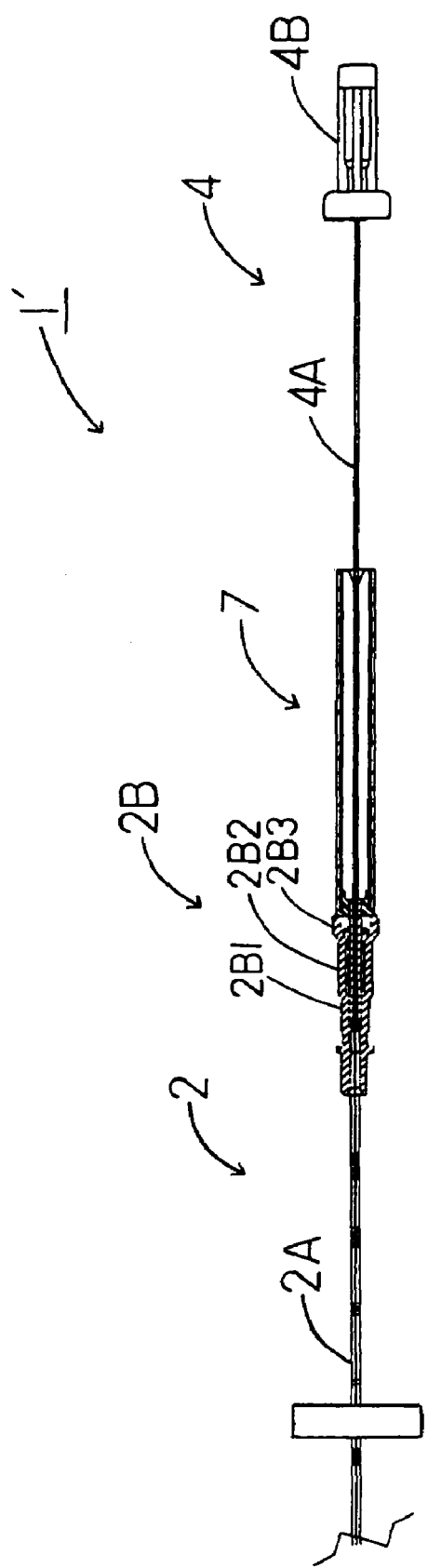
FIG. 10 is a schematic drawing of a therapeutic material delivery device 1' of the present invention.

FIG. 10 is a schematic drawing of one example of a therapeutic material delivery device 1' (to be abbreviated as "delivery device 1'" hereinafter) for delivery of a radioactive source, provided by the present invention.

The delivery device 1' shown in FIG. 10 is constituted of an outer needle 2 formed of an outer tubular needle 2A and an outer needle hub 2B supporting the outer tubular needle 2A, a cartridge 7 chargeable with a radioactive source 10 (see FIG. 11) that is to be connected thereto, and an inner needle 4 formed of a solid needle 4A and an inner needle hub 4B supporting the solid needle 4A.

In the above outer needle 2, the outer tubular needle 2A has a forward end that is sharpened so that it can be stuck into a body, and the end portion of the above outer tubular needle 2A is attached to the outer needle hub 2B. In the above outer needle hub 2B, preferably, a small-diameter portion 2B1, an intermediate-diameter portion 2B2 and a large-diameter portion 2B3 are integrally formed continuously from a forward end place to a backward end place for securing reliable engagement of the outer needle hub 2B with the forward end of the cartridge inserted when the cartridge is connected.

Figure 11:
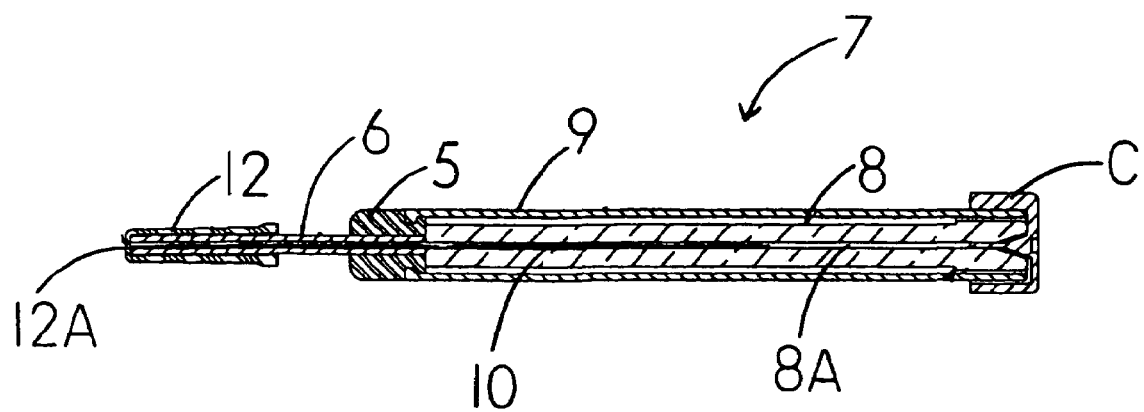
FIG. 11 is a cross-sectional view of a cartridge 7 of the present invention.

FIG. 11 is a cross-sectional view of a cartridge for use with the therapeutic material delivery device 1' shown in FIG. 10 (to be simply abbreviated as "cartridge" hereinafter), provided by the present invention. FIGS. 12(A), 12(B) and 12(C) are schematic drawings of components of the cartridge 7 shown in FIG. 11; FIG. 12(A) is a side view of forward end of the above outer tube 9, FIG. 12(B) is a cross-sectional view of the outer tube 9 in the longitudinal direction, and FIG. 9(C) is a schematic drawing of a cartridge body 8.

The cartridge 7 is constituted of a transparent cartridge body 8 that is for holding the above therapeutic material 10 inside and permits external visual observation thereof, and a shielding outer tube 9 that is fitted to the outer circumference of the cartridge body, is slidable in the longitudinal direction of the above cartridge and is made of a shielding material against radioactive rays.

The above shielding outer tube 9 (to be sometimes simply abbreviated as "outer tube 9" hereinafter) is made of a material that works as a shield against radioactive rays, and an engagement portion 9A may be formed in an inner circumference of the forward end thereof.

Figure 12:
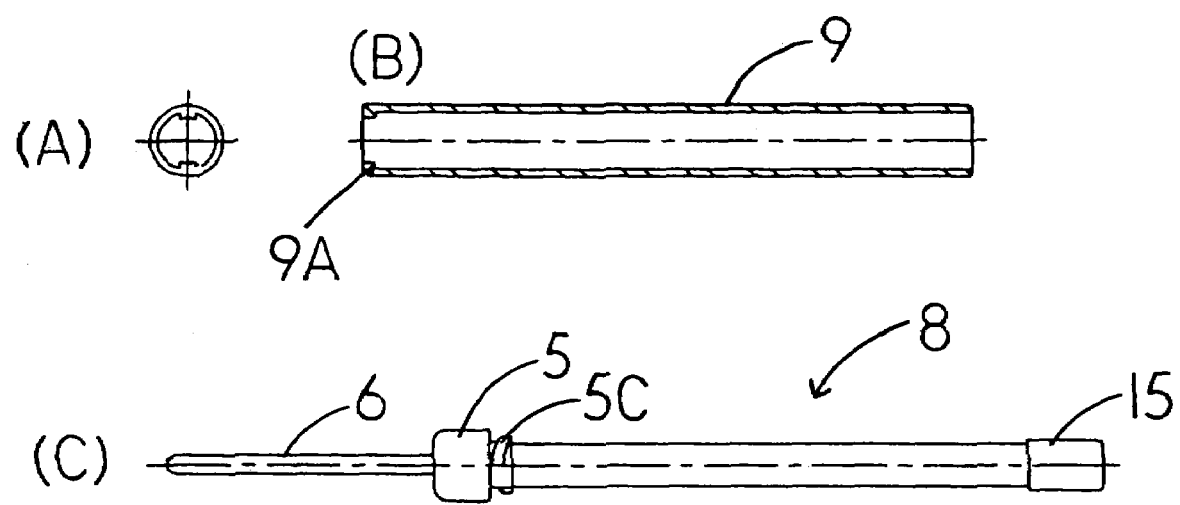
FIGS. 12(A), 12(B) and 12(C) are schematic drawings of components of the cartridge shown in FIG. 11.

In the above cartridge body 8, a space 8A for encasing the radioactive source 10 is formed in a central portion of the cartridge body 8 in the longitudinal direction. As shown in FIGS. 11 and 12, further, the forward end thereof is provided with a head portion 5, the backward end thereof is provided with a stopper 15, and the backward end of the above head portion 5 is provided with an engagement portion 5C that is to be engaged with the engagement portion 9A of the above outer tube 9.

The above head portion 5 supports a connector tube 6 whose forward end is formed in a tapered form, through the head portion, and the connector tube 6 is capped with a sheath 12 having an opening portion 12A having a smaller diameter than the outer diameter of the radioactive source 10 in the forward end thereof.

Since the above opening portion 12A has a smaller diameter than the outer diameter of the radioactive source, the radioactive source 10 does not easily come off the above opening portion 12A, and when the backward end of the radioactive source 10 is pushed and extruded with the forward end of the solid needle 4A, the radioactive source 10 can move toward the forward end of the outer needle 2 through the above opening portion 12A. The above sheath 12 is made of a soft material that is the same as, or similar to, that used for the already described sheath 5'.

As described already, the above cartridge body 8 is made of a material through which the radioactive source 10 charged and held inside can be visually observed from outside.

(Slide/Engagement Between Cartridge Body and Outer Tube)

In the cartridge 7, the outer tube 9 covers a circumference of the cartridge body 8. In this case, the engagement portion 5C of the backward end of the above head portion 5 and the engagement portion 9A of the forward end of the outer tube 9 are formed such that these engagement portions engage with each other. The backward end of the cartridge 7 is capped with a cap C which covers the outer tube 9.

Figure 13:
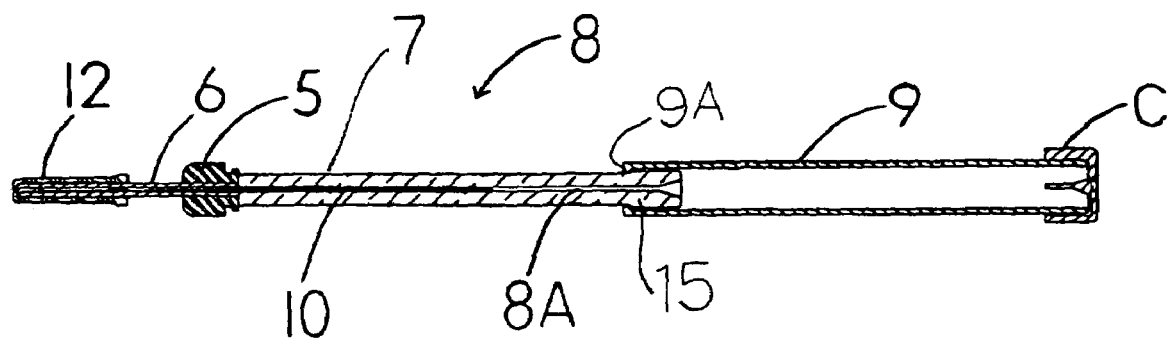
FIG. 13 is a schematic drawing for showing a state in which the outer tube 9 of the cartridge 7 is slid backward in the longitudinal direction and the cartridge body 8 is exposed.

FIG. 13 is a schematic drawing showing a state in which the outer tube 9 of the cartridge 7 is turned to slide it backwardly in the longitudinal direction and the cartridge body 8 is exposed.

When the radioactive source 10 charged in the cartridge body 8 is calibrated, the outer tube 9 is slid backwardly in the longitudinal direction to expose the cartridge body 8 (details thereof will be discussed later with reference to FIG. 15).

As shown in the schematic drawing of FIG. 13, when the outer tube 9 is slid in the longitudinal direction of the cartridge body to expose the cartridge body 8, the engagement portion 9A of the outer tube 9 is engaged with the forward end of the above stopper 15, so that there is no case where the outer tube 9 comes off the cartridge body 8.

Figure 14:
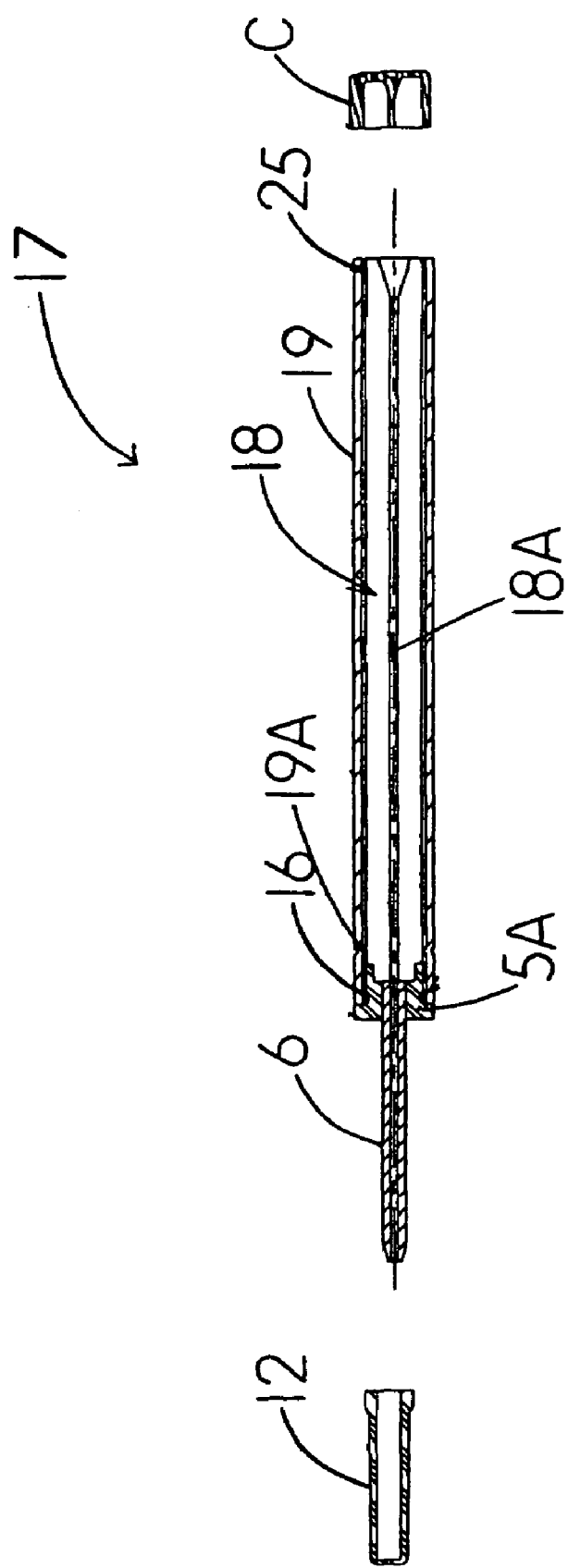
FIG. 14 is a cross-sectional view of a cartridge 17 that is another embodiment of the cartridge.

FIG. 14 is a cross-sectional view of a cartridge 17 that is other embodiment of the cartridge. FIG. 15 is a schematic drawing showing a state in which the outer tube 19 of the cartridge 17 is slid to expose the cartridge body 18.

The above cartridge 17 employs a constitution in which a stopper 16 is attached to the head portion 5A so that an outer tube 19 can be caught and stopped with the cartridge body 18 in place of forming the engagement portions 9A and 5C used for stopping the outer tube 9 in the cartridge body 8 like the above cartridge 7.

That is, the forward end of the cartridge body 18 is provided with a head portion 5A, and a stopper 16 having high frictional resistance is attached to a nearly central portion of the above head portion 5A. The stopper 16 is made of a material having high frictional resistance like elastomers such as rubber and silicone, and it is formed in the form of a band or a stripe having a cross-sectional form of a circle, an oval, a square, or the like. It is not necessarily required to form the stopper 16 on the entire outer circumference of the head portion 5A, and it may be formed at intervals or discontinuously so long as it can ensure sufficient frictional resistance.

Due to the frictional resistance between the above stopper 16 and the inner circumference of the forward end of the outer tube 19, the cartridge body 18 and the outer tube 19 are engaged with each other.

The above outer tube 19 is allowed to slide backwardly in the longitudinal direction, to expose the cartridge body 18. The surface of the inner circumference of forward portion of the outer tube 19 is provided with an engagement portion 19A similar to the already explained engagement portion 9A of the outer tube 9, so that the thus-provided engagement portion 19A is caught and stopped with a stopper 25 formed in the backward end of the cartridge body 18. There is therefore no case in which the above outer tube 19 comes off the cartridge body 18.

(Scale Marking and Calibration)

The surface of the cartridge body 18 of the above cartridge 17 is provided with a scale 20 for check of a length of the radioactive source 10. The scale indicates a length from the forward end of the connector tube 6. For example, in a case shown in FIG. 15, a division of 2 cm is marked on the end portion of the cartridge body 18, and divisions are provided up to 6 cm at intervals of 1 cm. Similarly, the cartridge bodies 8 and 28 of cartridges 7 and 27 may be provided with a scale.

The calibration of the radioactive source 10 held in the above cartridge body 18 will be explained with regard to the cartridge 17 as one example.

Figure 15:
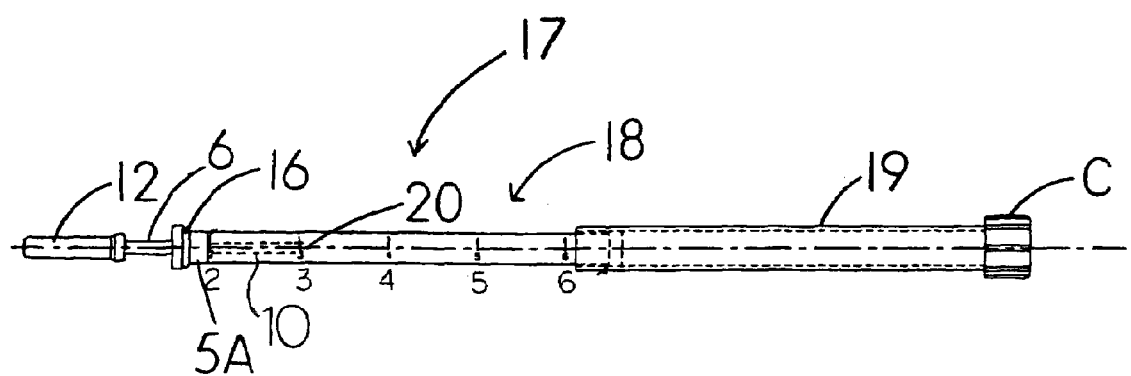
FIG. 15 is a schematic drawing for showing a state in which the outer tube 19 of the cartridge 17 is slid backward in the longitudinal direction and a cartridge body 18 is exposed.

As shown in FIG. 15, the above radioactive source 10 is positioned in the forward end of the connector tube 6 (position where the forward end of inner circumference of the sheath 12 is hit against), and the outer tube 19 is slid backwardly in the longitudinal direction.

When the radioactive source 10 is visually observed through the cartridge body 18 in the above case, and if the backward end of the radioactive source 10 is positioned at a division of 3, it is implied that the radioactive source 10 encased has a length of 3 cm. That is, that part of the radioactive source 10 charged in the above cartridge 17 which is exposed and externally visually observable in the cartridge body 18 has a length of only 1 cm. In this state, calibration is conducted, and the above 1 cm long part of the radioactive source is converted and calculated to the conclusion that the radioactive source having a radiation dose equivalent to 3 cm is charged.

In addition, the cartridge 7 shown in FIG. 11 can employ a constitution in which the cartridge body 8 is provided with a scale 20, and the radioactive source 10 charged can be calibrated in the same manner as above.

(Shielding Cartridge)

Figure 16:
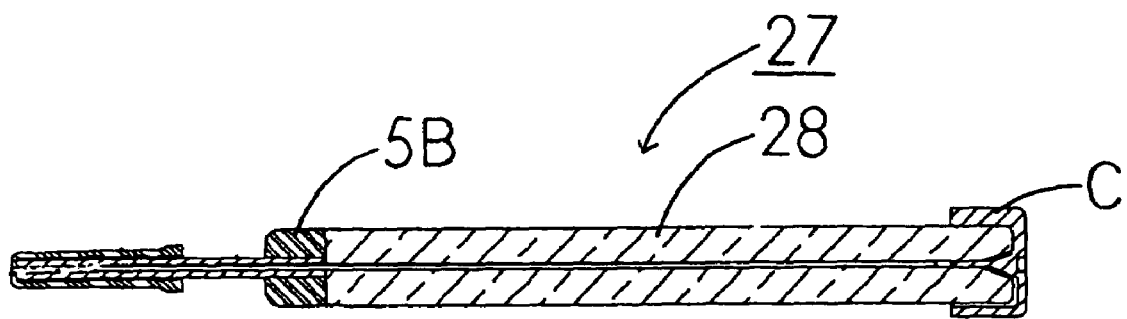
FIG. 16 is a cross-sectional view of a cartridge 27 that is another embodiment of the cartridge.

FIG. 16 is a cross-sectional view of a cartridge 27 that is another embodiment of the present invention.

The above cartridge 27 has a cartridge body 28 made of a material that is transparent and permits external visual observation (checking) of the radioactive source 10 and which itself can work as a shield against radioactive rays.

In this embodiment, the cartridge body 28 per se can work as a shield against radioactive rays without any shielding outer tube, so that the radioactive source that has been calibrated can be charged into the cartridge body 28 and a length of the radioactive source 10 can be checked without any radiation exposure.

(Radioactive Source Having a Small Length)

When the radioactive source 10 has a length of less than 2 cm, and if the radioactive source 10 is positioned in the forward end portion of the connector tube 6 of the cartridge 7 or 17 shown in FIG. 11 or 14, the radioactive source 10 completely disappears in the connector tube 6 and the head portion 5 or 5A of the cartridge body 8 or 18. There is therefore caused a problem that the calibration cannot be made in the above method.

Figure 17:
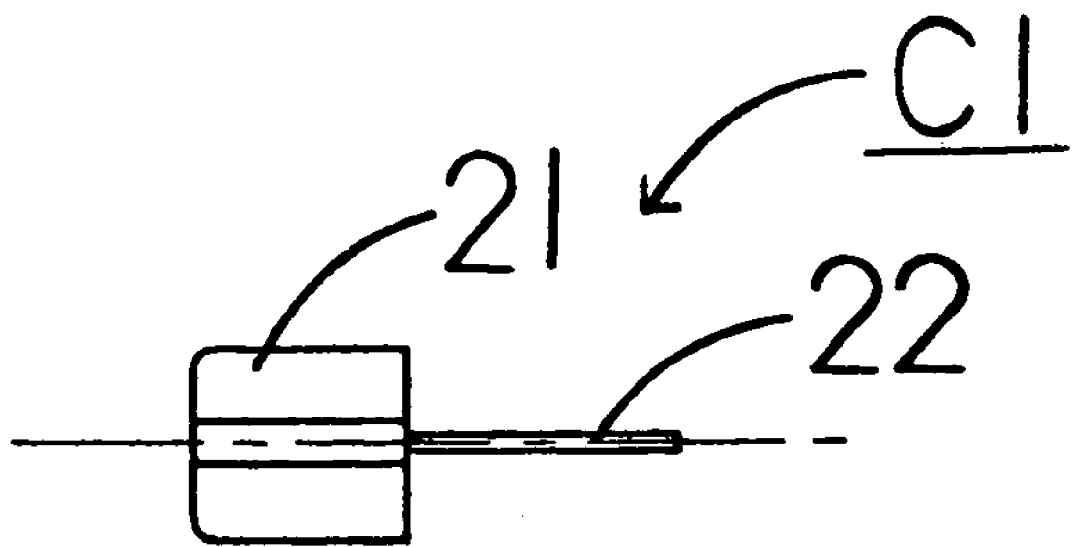
FIG. 17 is a schematic drawing of a cap C1.
Figure 18:
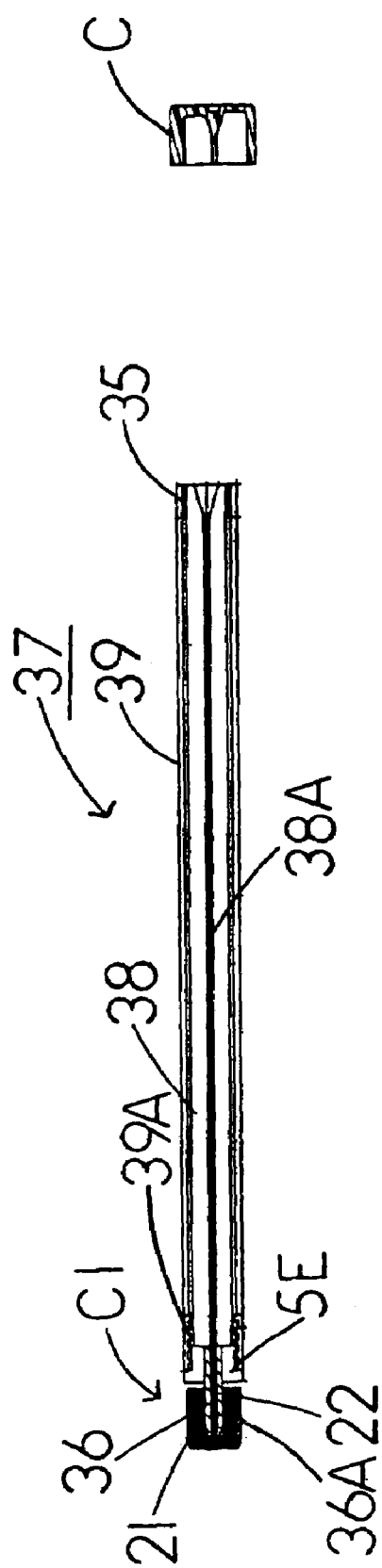
FIG. 18 is a cross-sectional view of a cartridge 37 of the present invention to which the cap C1 is attached.
Figure 19:
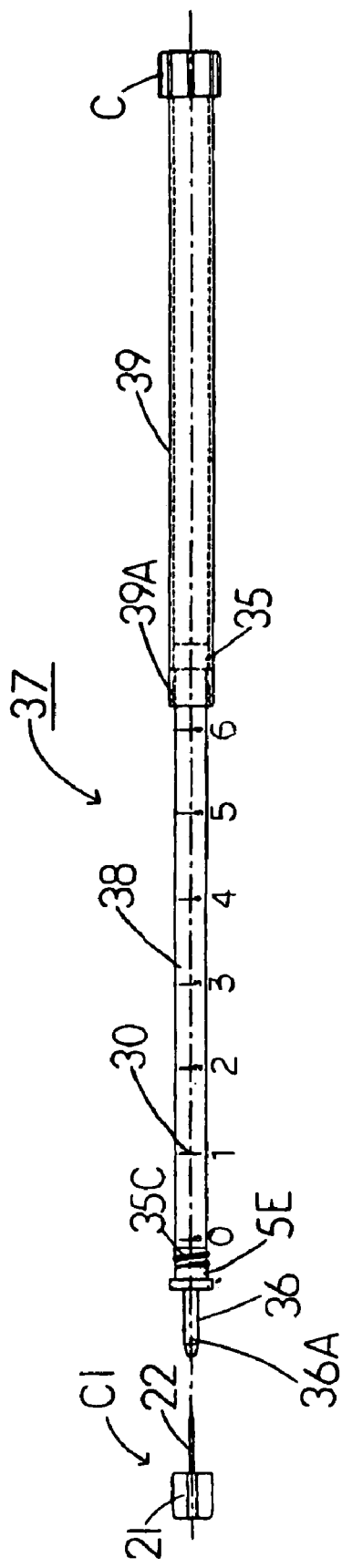
FIG. 19 is a schematic drawing for showing a state in which an outer tube 39 of the cartridge 37 is slid backward in the longitudinal direction and a cartridge body 38 is exposed.

FIGS. 17 to 19 show structures of a cartridge that permits the calibration of such a radioactive source having a small length. FIG. 17 is a cross-sectional view of a cap C1, FIG. 18 is a cross-sectional view of a cartridge 37 capped with the above cap C1, and FIG. 19 is a schematic drawing of a state in which an outer tube 39 of the above cartridge 37 is slid backwardly in the longitudinal direction and a cartridge body 38 is exposed.

The above cap C1 has a structure in which a spindle rod 22 is supported on the center of end portion of an inner circumference of a protection portion 21.

The above cartridge 37 is basically structured to have the same form as that of the above cartridge 7, and an outer tube 39 is attached to an outer circumference of the cartridge body 38. As shown in FIG. 19, the forward end of the cartridge body 38 is provided with a head portion 5E, and an engagement portion 35C is formed in the backward end of the above head portion 5E. Further, an engagement portion 39A is formed in the forward end of the outer tube 39, and these engagement portions 35C and 39A are formed to be engageable with each other.

The above cartridge 37 differs from the already explained cartridge 7 in that a connector tube 36 having a smaller length than the connector tube 6 is supported on the above head portion 5E. Another difference is that the surface of the cartridge body 38 is provided with a scale 30 that extends in the longitudinal direction from the forward place thereof to the backward place thereof and has divisions starting, for example, at 0 up to 6 cm at intervals of 1 cm.

As shown in FIG. 19, the spindle rod 22 of the above cap C1 is inserted into a passage 36A of the above connector tube 36, thereby to cap an outer circumference of the above connector tube 36 with an inner circumference of the protection portion 21. In this case, the length of the spindle rod or the length of insertion of the spindle rod into the passage 36A of the connector tube 36 is determined to position the forward end of the above spindle rod 22 at 0 of the scale 30 provided on the above cartridge body 38.

In this manner, the entire radioactive source 10 charged in the cartridge 37 appears in an encasing space 38A of the transparent cartridge body 38 and can be visually checked. Further, the forward end of the radioactive source 10 is brought into contact with the end portion of the spindle rod 22, whereby the forward end of the radioactive source 10 comes to 0 of the scale 30.

The calibration of the radioactive source 10 charged in the cartridge 37 is carried out by sliding the outer tube 39 backwardly in the longitudinal direction to expose the cartridge body 38 in the same manner as in the calibration of the radioactive source 10 charged in the above cartridge 7. That is, the entire length of the charged radioactive source 10 can be clearly visually observed, so that the entire radioactive source 10 is directly accurately calibrated.

When the cap 21 having the spindle rod 22 is used as described above, the radioactive source 10 having a small length as small as less than 2 cm can be calibrated and a conversion error can be avoided, so that a more accurate value can be determined.

The above technical idea can be applied to the cartridge 17 shown in FIG. 15. That is, in the cartridge 17, while the forms of the stopper 16 of the head portion 5A of the above cartridge body 18 and the outer tube 19 attached to the outer circumference of the cartridge body 18 are retained without any change, the connector tube 36 and the cap C1 as shown in FIG. 19 can be attached in place of the connector tube 6 and the sheath 12. As described above, when the surface of outer circumference of the cartridge body 18 shown in FIG. 15 is provided with a scale 30 having divisions starting, for example, at 0 cm up to 6 cm at intervals of 1 cm, the entire radioactive source 10 can be constantly calibrated irrespective of the length thereof, and, particularly, the radioactive source having a small length as small as less than. 2 cm can be easily calibrated.

(Implanting of Radioactive Source)

The procedures of implanting a radioactive source in a body with a therapeutic material delivery device having the cartridge of the present invention will be explained with drawings.

Figure 20:
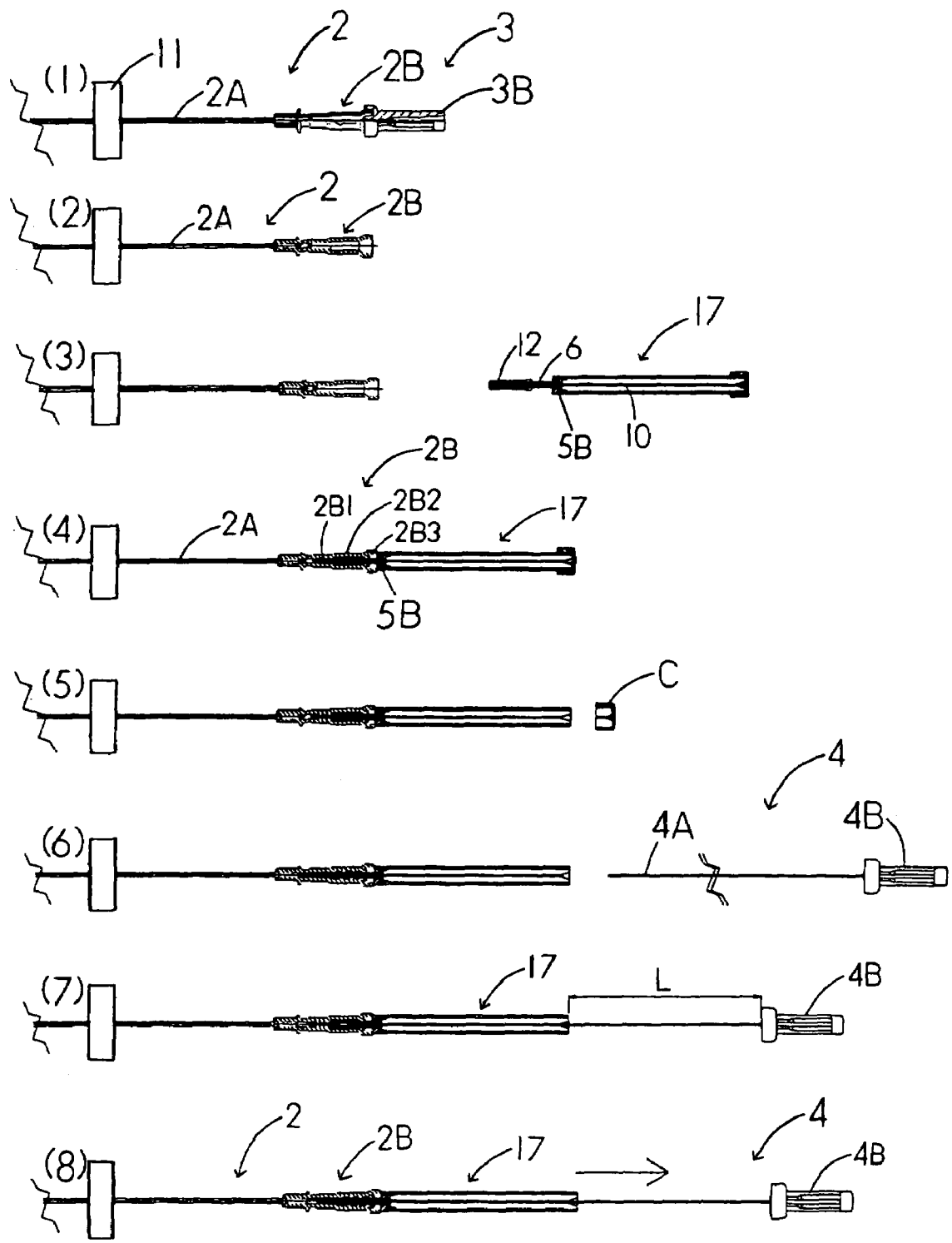
FIG. 20 shows schematic drawings for explaining procedures of embedding radioactive sources 10 in the interior of a body with a delivery device using the cartridge 17 of the present invention.

FIG. 20 is a schematic drawing (partial cross-sectional view) for showing one example of the procedures of implanting the radioactive source 10 in a body, for example, with the delivery device 1' having the cartridge 17 of the present invention. Further, the same procedures can be employed for handling the above cartridges 7 and 27. In addition, the following (1) to (8) corresponds to (1) to (8) in FIG. 20.

(1) For determining the sticking position of the outer needle 2, a plate 11 for implanting the therapeutic material (radioactive source) (to be sometimes abbreviated as "implanting plate 11" hereinafter) is arranged. The above outer needle 2 (outer tubular needle 2A) is stuck in a sticking hole (intended position) of the above implanting plate 11. The above outer needle 2 has the middle needle 3 inserted therein. The outer needle 2 that has stuck is monitored with an ultrasonic diagnosis apparatus inserted through an anus, to determine a position of the radioactive source.

In this embodiment, the above middle needle 3 not only works as a reinforcement when the outer needle 2 is stuck in a body, but also is inserted into the outer needle 2 for preventing the spurt of body fluids such as blood and breakage of internal tissues. It is therefore preferred to use a middle solid needle as the above middle tubular needle 3A to be supported by the middle needle hub 3B of the middle needle 3. The middle tubular needle 3A that can work as a reinforcement may be used since the spurt of body fluids can be prevented by attaching a stopper to the middle needle hub 3B. In the present invention, therefore, the middle tubular needle 3A includes the above middle solid needle when the middle needle 3 is used for the same purpose as that in this embodiment.

(2) In a state where the outer tubular needle 2A is kept being stuck, the middle needle 3 is withdrawn from the above outer needle 2.

(3) There is prepared beforehand the cartridge 17 that is charged with the radioactive source 10 to be implanted in a body and is finished with calibration of a radiation dose.

(4) The forward end of the above cartridge 17 is connected to the outer needle hub 2B supporting the outer tubular needle 2A.

That is, specifically, the outer needle hub 2B is formed by continuously integrating a small-diameter portion 2B1, an intermediate-diameter portion 2B2 and a large-diameter portion 2B3, and the above sheath 12 is fitted in an inner circumference of the intermediate-diameter portion 2B2. Further, the above cartridge 17 is pressed to bring the forward end of the head portion 5A into contact with the large-diameter portion 2B3. And, the forward end of the connector tube 6 is projected from the opening portion 12A of the sheath 12, and the outer circumference of forward end of the above connector tube 6 is engaged with the inner circumference of the small-diameter portion 2B1, so that the encasing space 18A of the cartridge body 18 and the outer tubular needle 2A communicate with each other.

(5) The cap C capped on the backward end of the cartridge 17 is removed, to be ready for insertion of the inner needle 4 into the above cartridge.

(6) The inner needle 4 is newly inserted through the backward end of the cartridge 17, to extrude the radioactive source 10 charged in the cartridge. The forward end of the cartridge 17 is engaged with the outer needle hub 2B of the outer needle 2, and the solid needle 4A is inserted and moved forward until the backward end of the above cartridge 17 and the forward end of the above inner needle hub 4B come to be engaged with each other. In this case, the above therapeutic material 10 is extruded through the forward end of the outer tubular needle 2A with the solid needle 4A to be completely exposed. For this purpose, preferably, the above solid needle 4A is formed so as to have a larger length than the above outer tubular needle 2A.

(7) When the forward end of the above radioactive source 10 is implanted in an intended portion in a body through the outer needle 2, and when the backward end of the radioactive source 10 moves to reach the forward end of the above outer needle 2 (that is, when the distance from the forward end of the inner needle hub 4b of the inserted inner needle 4 to the backward end of the cartridge 17 is a length L equivalent to the length of the radioactive source 10), the extrusion with the inner needle 4 is stopped.

(8) The inner needle hub 4B is fixed, and the outer needle 2 and the cartridge 17 are pulled in the direction of the inner needle hub 4B, whereby the radioactive source 10 is implanted in a body. Thereafter, the outer needle 2, the cartridge 17 and the inner needle 4 are withdrawn from the interior of the body.

Figure 21:
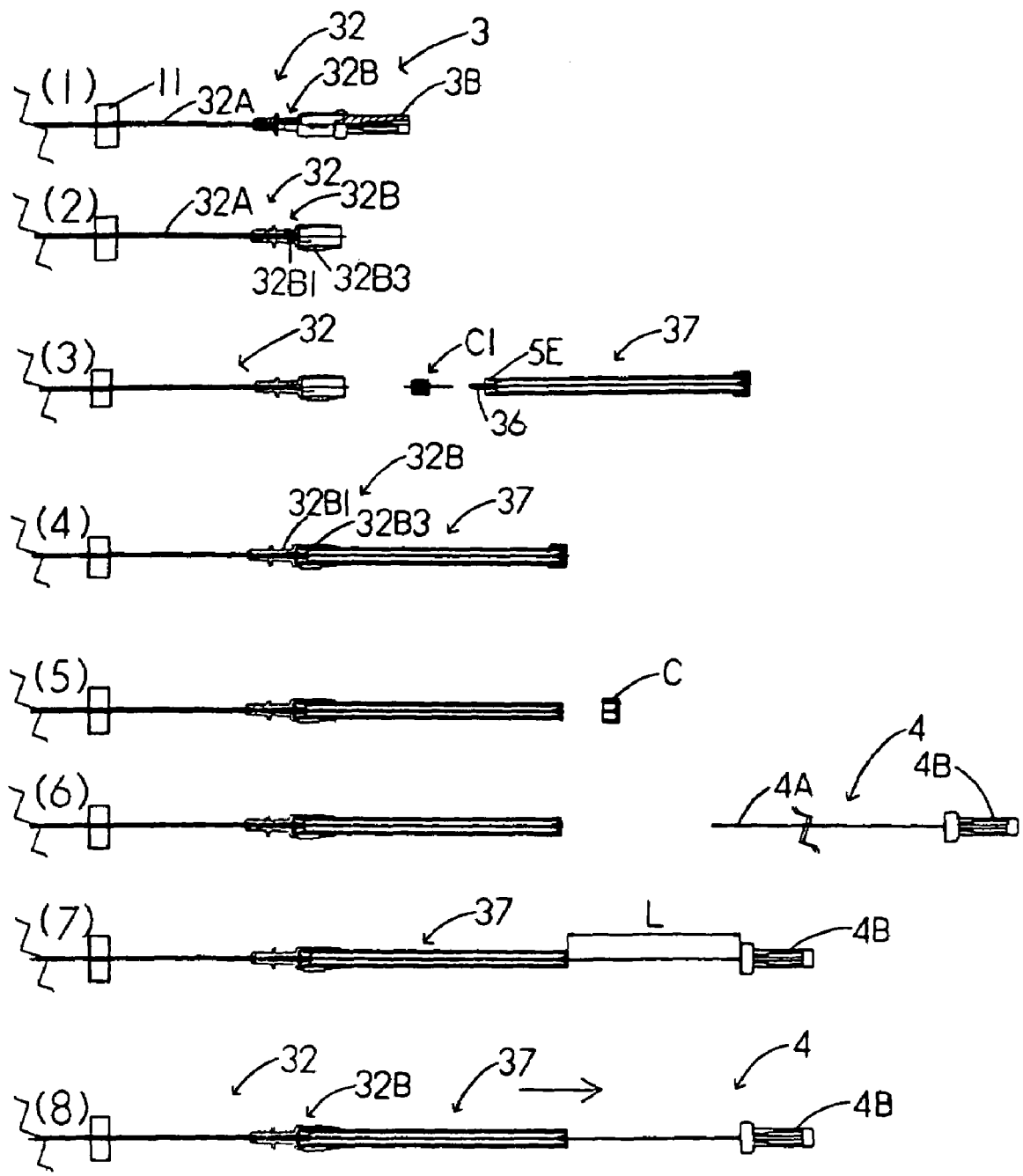
FIG. 21 shows schematic drawings for explaining procedures of embedding radioactive sources 10 in the interior of a body with a delivery device using the cartridge 37 of the present invention.

FIG. 21 is a schematic drawing (partial cross-sectional view) for showing one example of the procedures of implanting the radioactive source 10 in a body with the delivery device 1' using the cartridge 37 that is another type in the present invention.

When the cartridge 37 is used, the procedures are carried out almost in the same manner as in the above procedures using the cartridge 17, so that the procedures will be explained only with regard to those parts that are different from the procedures using the cartridge 17.

As already discussed, the calibration of the entire radioactive source 10 can be carried out beforehand with regard to the above cartridges 7 and 17 by replacing the connector tube 6 and the sheath 12 with the connector tube 36 and the cap C1 and further providing the surface of outer circumference of each of the cartridge bodies 8 and 18 with a scale having divisions starting at 0 cm up to 6 cm at intervals of 1 cm. The above radioactive source 10 can be implanted in a body by the same procedures as those shown in FIG. 20.

(1) In the same manner as in FIG. 20(1), the above outer needle 32 (outer tubular needle 32A) is stuck in the sticking hole (intended position) of the implanting plate 11. In the above outer needle 32, the middle needle 3 having a middle solid needle supported by the middle needle hub 3B is kept inserted.

As already described, the above middle needle 3 works as a reinforcement when the outer needle 32 is stuck in a body, and it is inserted into the outer needle 32 for preventing the spurt of body fluids such as blood and breakage of internal tissues.

(2) The middle needle 3 is withdrawn from the above outer needle 32. The above outer needle 32 has the outer needle hub 32B supporting the outer tubular needle 32A, and the above outer needle hub 32B has a small-diameter portion 32B1 in a forward place and a large-diameter portion 32B3 in a backward place which portions are integrally formed.

(3) There is prepared beforehand the cartridge 37 that is charged with the radioactive source 10 to be implanted in a body and is finished with calibration of a radiation dose and from which the cap C1 is removed. The cartridge 37 is held horizontally.

(4) The forward end of the above cartridge 37 is connected to the backward end of the outer needle hub 32B. That is, the forward end of the head portion 5E comes in contact with the large-diameter portion 32B3, and the outer circumference of forward end of the above connector tube 36 comes to be engaged with the inner circumference of the small diameter portion 32B1, so that the encasing space 38A of the cartridge body 38 and the outer tubular needle 32A come to communicate with each other. The procedures (5) to (8) thereafter are basically the same as those of handling the cartridge 17 explained with reference to FIG. 20, so that detailed explanations thereof are omitted.

(Effect of the Invention)

(I) According to the protective tool of the present invention or the delivery device having the protective tool, attaching the protective tool 68A or 68B to the outer needle 2 can produces effects that wrong or accidental sticking of the outer tubular needle 2A after use is prevented and that no blood adhering to the above outer tubular needle is dissipated.

(II) Further, according to the cartridge of the present invention or the delivery device using the cartridge, the following effects are produced.

(a) The cartridge 7 or 17 of the present invention having the outer tube 9 or 19 obviates the calibration of a radioactive source before the radioactive source is charged in the cartridge. The radioactive source 10 charged in the cartridge can be directly calibrated without exposing the radioactive source 10.

(b) The cartridge 7, 17, 27 or 37 of the present invention has a head portion 5, 5A, 5B or 5E formed in the forward end thereof, and the connector tube 6 or 36 is supported through the above head portion, so that the above connector tube 6 or 36 does not break or bend under a lateral strong force.

(c) The above connector tube 6 is capped with the sheath 12 having the opening portion 12A formed, and the sheath 12 is engaged with the inner wall of the outer needle hub 2B of the outer needle 2, so that the radioactive source 10 charged in the cartridge 7, 17 or 27 of the present invention can be extruded to the forward end of the outer needle 2 without resistance.

(d) The outer circumference of the cartridge body 8, 18 or 28 of the cartridge 7, 17 or 27 of the present invention is provided with the scale 20, so that the radioactive source can be externally visually checked for a length. Further, on the basis of the above scale, the converted value of calibration of the radioactive source 10 can be obtained.

(e) According to the cartridge 37 of the present invention in which the connector tube 36 supported on the forward end of the cartridge body 38 is capped with the cap C1, the surface of outer circumference of the cartridge body 38 is provided with the scale 30 having divisions starting at 0 cm up to 6 cm at intervals of 1 cm and the outer tube 39 is attached to the outer circumference, the entire radioactive source 10 can be directly calibrated, so that an error caused by conversion can be avoided.

(f) The cartridge body 28 of the cartridge 27 of the present invention is made of a material that permits external visual observation of the radioactive source and can work as a shield against radioactive rays, so that the charged radioactive source 10 can be externally easily checked for a length without exposure to radioactive rays.

What is claimed is:

1. A protective tool for a therapeutic material delivery device comprising an outer needle having an outer tubular needle and an outer needle hub supporting the outer tubular needle, the protective tool being configured to be attached to said outer needle for the protection thereof, the protective tool comprising a cover and a cap or stopper attached to a forward end of said cover for protecting the forward end of the outer tubular needle, wherein said cover is formed of a plurality of tubes having different diameters that are formed so as to consecutively decrease from a forward place to the outer needle hub in a backward place, and said tubes are thereby connected such that the cover is extendable in the longitudinal direction, wherein said cap has an inner tube formed inside, said inner tube has, made in a bottom thereof, a hole for inserting and passing said outer tubular needle, and said inner tube has, formed in an outer circumference, a groove portion for inserting a forward end of said outer tubular needle.

2. A protective tool for a therapeutic material delivery device comprising an outer needle having an outer tubular needle and an outer needle hub supporting the outer tubular needle, the protective tool being configured to be attached to said outer needle for the protection thereof, the protective tool comprising a cover and a cap or stopper attached to a forward end of said cover for protecting the forward end of the outer tubular needle, wherein said cover is formed of a plurality of tubes having different diameters that are formed so as to consecutively decrease from a forward place to the outer needle hub in a backward place, and said tubes are thereby connected such that the cover is extendable in the longitudinal direction, wherein said stopper is constituted of a tubular opening/closing portion having a forward end and a connector portion, said opening/closing portion has slits formed in the longitudinal direction, one in an upper portion and the other in a lower portion, said forward end has an opening portion, and said connector portion has pressing portions formed, one on the right and the other on the left, and has cutout grooves formed, one in an upper place and the other in a lower place.

3. A protective tool for a therapeutic material delivery device comprising an outer needle having an outer tubular needle and an outer needle hub supporting the outer tubular needle, a middle needle having a middle tubular needle and a middle needle hub supporting the middle tubular needle and an inner needle having a solid needle and an inner needle hub supporting the solid needle, the outer needle, the middle needle and the inner needle being to be connected for use, the protective tool being configured to be attached to said outer needle for the protection thereof, which protective tool comprises a cover and a cap or a stopper that is attached to the forward end of said cover for protecting the forward end of said outer tubular needle, wherein said cover is formed of a plurality of tubes having different diameters that are formed so as to consecutively decrease from a forward place to the outer needle hub in a backward place, and said tubes are thereby connected such that the cover is extendable in the longitudinal direction, wherein said cap has an inner tube formed inside, said inner tube has, in a bottom thereof, a hole for inserting and passing said outer tubular needle, and said inner tube has, formed in an outer circumference thereof, a groove portion for inserting the forward end of said outer tubular needle.

4. A protective tool for a therapeutic material delivery device comprising an outer needle having an outer tubular needle and an outer needle hub supporting the outer tubular needle, a middle needle having a middle tubular needle and a middle needle hub supporting the middle tubular needle and an inner needle having a solid needle and an inner needle hub supporting the solid needle, the outer needle, the middle needle and the inner needle being configured to be connected for use, the protective tool being configured to be attached to said outer needle for the protection thereof, which protective tool comprises a cover and a cap or a stopper that is attached to the forward end of said cover for protecting the forward end of said outer tubular needle, wherein said cover is formed of a plurality of tubes having different diameters that are formed so as to consecutively decrease from a forward place to the outer needle hub in a backward place, and said tubes are thereby connected such that the cover is extendable in the longitudinal direction, wherein said stopper is constituted of a tubular opening/closing portion having a forward end and a connector portion, said opening/closing portion has slits formed in the longitudinal direction, one in an upper portion and the other in a lower portion, said forward end has an opening portion, and said connector portion has pressing portions formed, one on the right and the other on the left, and has cutout grooves formed, one in an upper place and the other in a lower place.

* * * * *